US006788965B2

(12) United States Patent
Ruchti et al.

(10) Patent No.: US 6,788,965 B2
(45) Date of Patent: Sep. 7, 2004

(54) INTELLIGENT SYSTEM FOR DETECTING ERRORS AND DETERMINING FAILURE MODES IN NONINVASIVE MEASUREMENT OF BLOOD AND TISSUE ANALYTES

(75) Inventors: Timothy L. Ruchti, Gilbert, AZ (US); Christopher C. Briggs, Chandler, AZ (US); Thomas B. Blank, Chandler, AZ (US); Alexander D. Lorenz, Phoenix, AZ (US); Mutua Mattu, Gilbert, AZ (US); Marcy Makarewicz, Chandler, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 0 days.

(21) Appl. No.: 10/211,478

(22) Filed: Aug. 1, 2002

(65) Prior Publication Data

US 2003/0060692 A1 Mar. 27, 2003

Related U.S. Application Data

(60) Provisional application No. 60/310,033, filed on Aug. 3, 2001.

(51) Int. Cl.[7] .............................................. A61B 5/00
(52) U.S. Cl. ..................... 600/316; 600/322; 600/310; 600/473; 600/476
(58) Field of Search ................... 600/310, 322, 600/316, 323, 326, 336, 473, 476; 356/39, 300; 128/920, 925; 702/19

(56) References Cited

U.S. PATENT DOCUMENTS 6,526,299 B2 * 2/2003 Pickard ...................... 600/310

* cited by examiner

Primary Examiner—Eric F. Winakur
(74) Attorney, Agent, or Firm—Glenn Patent Group; Michael A. Glenn

(57) ABSTRACT

An intelligent system for detecting errors and determining failure modes operates on an absorbance spectrum of in vivo skin tissue. Application of the system results in improved prediction accuracy through rejection of invalid and poor samples. System components include a noninvasive blood glucose meter, such as a near IR spectrometer, an error detection system (EDS); a system for diagnosing and mitigating errors; and a reporting method. In the EDS, a pattern classification engine and hierarchy of levels analyzes, detects and diagnoses instrument, interface and sample errors manifested in the spectrum to determine suitability of an absorbance spectrum for blood glucose measurement. The final component of the system evaluates the error condition, diagnoses the specific mode of failure (if necessary) and reports actions to be taken. Sub-components and levels of the EDS can operate independently of the other system elements to the benefit of a noninvasive glucose measurement system.

124 Claims, 16 Drawing Sheets

INTELLIGENT SYSTEM FOR DETECTING ERRORS AND DETERMINING FAILURE MODES IN NONINVASIVE MEASUREMENT OF BLOOD AND TISSUE ANALYTES

CROSS REFERENCE TO RELATED APPLICATION

This application claims benefit of U.S. Provisional Patent Application Ser. No. 60/310,033, filed on Aug. 3, 2001.

BACKGROUND OF THE INVENTION

1. Field of the Invention

The present invention relates generally to noninvasive blood and tissue analyte determination. More particularly, the invention relates to methods and apparatus for detecting conditions leading to erroneous noninvasive tissue analyte measurements.

2. Description of Related Art

Previously we reported an invention for measuring glucose noninvasively through an intelligent measurement system (IMS) in S. Malin, T. Ruchti, An intelligent system for noninvasive blood analyte prediction, U.S. Pat. No. 6,280,381 (Aug. 28, 2001). The IMS involved the classification of patients into a multiplicity of "bins" or "classes" and the application of a suitable calibration model. A key element of the IMS is a Performance Monitor capable of detecting poor instrument performance, patient sampling errors, and other anomalies leading to an invalid or degraded glucose measurement. Here we describe a novel method for detecting and mitigating the wide range of potential errors associated with the in vivo application of an instrument for the noninvasive measurement of glucose.

The error detection system (EDS) operates on a near infrared measurement of in vivo skin tissue. The architecture employs a pattern classification engine and hierarchy of levels to analyze, detect, and diagnose instrument, interface, and sample errors manifested in the near infrared measurement. A priori information about the sources of errors is used to establish preset limits and categories of errors. Application of the system results in improved noninvasive glucose measurement accuracy through the rejection of invalid and poor samples.

Noninvasive Measurement of Glucose

Diabetes is a leading cause of death and disability worldwide and afflicts an estimated 16 million Americans. Complications of diabetes include heart and kidney disease, blindness, nerve damage, and high blood pressure with the estimated total cost to United States economy alone exceeding $90 billion per year [*Diabetes Statistics,* Publication No. 98-3926, National Institutes of Health, Bethesda Md. (November 1997)]. Long-term clinical studies show that the onset of complications can be significantly reduced through proper control of blood glucose levels [The Diabetes Control and Complications Trial Research Group, *The effect of intensive treatment of diabetes on the development and progression of long-term complications in insulin-dependent diabetes mellitus.* N Eng J of Med, 329:977–86 (1993)]. A vital element of diabetes management is the self-monitoring of blood glucose levels by diabetics in the home environment. A significant disadvantage of current monitoring techniques is that they discourage regular use due to the inconvenient and painful nature of drawing blood through the skin prior to analysis. Therefore, new methods for self-monitoring of blood glucose levels are required to improve the prospects for more rigorous control of blood glucose in diabetic patients.

Numerous approaches have been explored for measuring glucose levels in vivo, ranging from invasive methods such as micro dialysis to noninvasive technologies that rely on spectroscopy. Each method has associated advantages and disadvantages, but only a few have received approval from certifying agencies. To date, no noninvasive techniques for the self-monitoring of blood glucose have been certified.

One method, near-infrared spectroscopy involves the illumination of a spot on the body with near-infrared electromagnetic radiation (light in the wavelength range 700–0.2500 nm). The light is partially absorbed and scattered, according to its interaction with the constituents of the tissue prior to being reflected back to a detector. The detected light contains quantitative information that is based on the known interaction of the incident light with components of the body tissue including water, fats, protein, and glucose.

Previously reported methods for the noninvasive measurement of glucose through near-infrared spectroscopy rely on the detection of the magnitude of light attenuation caused by the absorption signature of blood glucose as represented in the targeted tissue volume. The tissue volume is the portion of irradiated tissue from which light is reflected or transmitted to the spectrometer detection system. The signal due to the absorption of glucose is extracted from the spectral measurement through various methods of signal processing and one or more mathematical models. The models are developed through the process of calibration on the basis of an exemplary set of spectral measurements and associated reference blood glucose values (the calibration set) based on an analysis of capillary (fingertip), or venous blood.

Near-infrared spectroscopy has been demonstrated in specific studies to represent a feasible and promising approach to the noninvasive prediction of blood glucose levels. M. Robinson, R. Eaton, D. Haaland, G. Keep, E. Thomas, B. Stalled, P. Robinson, Noninvasive *glucose monitoring in diabetic patients: A preliminary evaluation,* Clin Chem, 38:1618–22 (1992) reports three different instrument configurations for measuring diffuse transmittance through the finger in the 600–1300 nm range. Meal tolerance tests were used to perturb the glucose levels of three subjects and calibration models were constructed specific to each subject on single days and tested through cross-validation. Absolute average prediction errors ranged from 19.8 to 37.8 mg/dL. H. Heise, R. Marbach, T. Koschinsky, F. Gries, Noninvasive *blood glucose sensors based on near-infrared spectroscopy,* Artif Org, 18:439–47 (1994); H. Heise, R. Marbach, *Effect of data pretreatment on the noninvasive blood glucose measurement by diffuse reflectance near-IR spectroscopy,* SPIE Proc, 2089:114–5 (1994); R. Marbach, T. Koschinsky, F. Gries, H. Heise, Noninvasive *glucose assay by near-infrared diffuse reflectance spectroscopy of the human inner lip,* Appl Spectrosc, 47:875–81 (1993) and R. Marbach, H. Heise, *Optical diffuse reflectance accessory for measurements of skin tissue by near-infrared spectroscopy,* Applied Optics 34(4):610–21 (1995) present results through a diffuse reflectance measurement of the oral mucosa in the 1111–1835 nm range with an optimized diffuse reflectance accessory. In vivo experiments were conducted on single diabetics using glucose tolerance tests and on a population of 133 different subjects. The best standard error of prediction reported was 43 mg/dL and was obtained from a two-day single person oral glucose tolerance test that was evaluated through cross-validation.

K. Jagemann, C. Fischbacker, K. Danzer, U. Muller, B. Mertes, *Application of near-infrared spectroscopy for non-*

*invasive determination of blood/tissue glucose using neural network,* Z Phys Chem, 191 S: 179–190 (1995); C. Fischbacker, K. Jagemann, K. Danzer, U. Muller, L. Papenkrodt, J. Schuler, *Enhancing calibration models for noninvasive near-infrared spectroscopic blood glucose determinations,* Fresenius J Anal Chem 359:78–82 (1997); K. Danzer, C. Fischbacker, K. Jagemann, K. Reichelt, *Near-infrared diffuse reflection spectroscopy for noninvasive blood-glucose monitoring,* LEOS Newsletter 12(2):9–11 (1998); and U. Muller, B. Mertes, C. Fischbacker, K. Jagemann, K. Danzer, *Noninvasive blood glucose monitoring by means of new infrared spectroscopic methods for improving the reliability of the calibration models,* Int J Artif Organs, 20:285–290 (1997) recorded spectra in diffuse reflectance over the 800–1350 nm range on the middle finger of the right hand with a fiber-optic probe. Each experiment involved a diabetic subject and was conducted over a single day with perturbation of blood glucose levels through carbohydrate loading. Results, using both partial least squares regression and radial basis function neural networks were evaluated on single subjects over single days through cross-validation. Danzer, et al., supra, report an average root mean square prediction error of 36 mg/dL through cross-validation over 31 glucose profiles.

J. Burmeister, M. Arnold, G. Small, *Human noninvasive measurement of glucose using near infrared spectroscopy* [abstract], Pittcon, New Orleans La. (1998) collected absorbance spectra through a transmission measurement of the tongue in the 1429–2000 nm range. A study of five diabetic subjects was conducted over a 39-day period with five samples taken per day. Every fifth sample was used for an independent test set and the standard error of prediction for all subjects was greater than 54 mg/dl.

In T. Blank, T. Ruchti, S. Malin, S. Monfre, *The use of near-infrared diffuse reflectance for the noninvasive prediction of blood glucose,* IEEE Lasers and Electro-Optics Society Newsletter, 13:5 (October 1999), the reported studies demonstrate noninvasive measurement of blood glucose during modified oral glucose tolerance tests over a short time period. The calibration was customized for the individual and tested over a relatively short time period.

In all of these studies, limitations were cited that would affect the acceptance of such a method as a commercial product. These limitations included sensitivity, sampling problems, time lag, calibration bias, long-term reproducibility, and instrument noise. Fundamentally, however, accurate noninvasive estimation of blood glucose is presently limited by the available near-infrared technology, the trace concentration of glucose relative to other constituents and the dynamic nature of the skin and living tissue of the patient (for example, see O. Khalil, *Spectroscopic and clinical aspects of noninvasive glucose measurements,* Clin Chem, 45:165–77 (1999)). As reported by S. Malin, T. Ruchti, An Intelligent System for Noninvasive Blood Analyte Prediction, U.S. Pat. No. 6,280,381 (Aug. 28, 2001), the entirety of which is hereby incorporated by reference, chemical, structural, and physiological variations occur that produce dramatic and nonlinear changes in the optical properties of the tissue sample [see R. Anderson, J. Parrish, *The optics of human skin,* Journal of Investigative Dermatology, 7:1, pp.13–19 (1981), W. Cheong, S. Prahl, A. Welch, *A review of the optical properties of biological tissues,* IEEE Journal of Quantum Electronics, 26:12, pp.2166–2185, (December 1990), D. Benaron, D. Ho, *Imaging (NIRI) and quantitation (NIRS) in tissue using time-resolved spectrophotometry: the impact of statically and dynamically variable optical path lengths,* SPIE, 1888, pp.10–21 (1993), J. Conway, K. Norris, C. Bodwell, *A new approach for the estimation of body composition: infrared interactance,* The American Journal of Clinical Nutrition, 40, pp.1123–1140 (December 1984), S. Homma, T. Fukunaga, A. Kagaya, *Influence of adipose tissue thickness in near infrared spectroscopic signals in the measurement of human muscle,* Journal of Biomedical Optics, 1:4, pp.418–424 (October 1996), A. Profio, *Light transport in tissue,* Applied Optics, 28:12), pp. 2216–2222, (June 1989), M. Van Gemert, S. Jacques, H. Sterenborg, W. Star, *Skin optics,* IEEE Transactions on Biomedical Engineering, 36:12, pp.1146–1154 (December 1989), and B. Wilson, S. Jacques, *Optical reflectance and transmittance of tissues: principles and applications,* IEEE Journal of Quantum Electronics, 26:12, pp. 2186–2199].

The measurement is further complicated by the heterogeneity of the sample, the multi-layered structure of the skin, and the rapid variation related to hydration levels, changes in the volume fraction of blood in the tissue, hormonal stimulation, temperature fluctuations, and blood analyte levels. This can be further considered through a discussion of the various properties of the skin, sample error, and instrumentation related issue.

Tissue Properties

Skin Structure

The structure and composition of skin varies widely among individuals as well as between different sites and over time on the same individual. Skin consists of a superficial layer known as the stratum corneum, a stratified cellular epidermis, and an underlying dermis of connective tissue. Below the dermis is the subcutaneous fatty layer or adipose tissue. The epidermis, with a thickness of 10–150 $\mu$m, together with the stratum corneum provides a barrier to infection and loss of moisture, while the dermis is the thick inner layer that provides mechanical strength and elasticity [F. Ebling, *The Normal Skin, Textbook of Dermatology,* $2^{nd}$ ed.; A. Rook; D. Wilkinson, F. Ebling, Eds.; Blackwell Scientific, Oxford, pp 4–24 (1972)]. In humans, the thickness of the dermis ranges from 0.5 mm over the eyelid to 4 mm on the back and averages approximately 1.2 mm over most of the body [S. Wilson, V. Spence, Phys. Med. Biol., 33:894–897 (1988)].

In the dermis, water accounts for approximately 70% percent of the volume. The next most abundant constituent is collagen, a fibrous protein comprising 70–75% of the dry weight of the dermis. Elastin fibers, also a protein, are plentiful though they constitute only a small proportion of the bulk. In addition, the dermis contains a wide variety of structures (e.g., sweat glands, hair follicles and blood vessels) and other cellular constituents [see F. Ebling, supra]. Conversely, the subcutaneous layer (adipose tissue) is by volume approximately 10% water and consists primarily of cells rich in triglycerides (fat). The concentration of glucose varies in each layer according to the water content, the relative sizes of the fluid compartments, the distribution of capillaries and the perfusion of blood. Due to the high concentration of fat, the average concentration of glucose in subcutaneous tissue is significantly lower than that of the dermis.

Scattering Properties of Skin

When a beam of light beam is directed onto the skin surface, a part of it is reflected while the remaining part penetrates the skin. The proportion of reflected light energy is strongly dependent on the angle of incidence. At nearly perpendicular incidence, about 4% of the incident beam is reflected due to the change in refractive index between air ($\eta_D$=1.0) and dry stratum corneum ($\eta_D$=1.55). For normally incident radiation, this "specular reflectance" component may be as high as 7%, because the very rigid and irregular surface of the stratum corneum produces off-normal angles of incidence. Regardless of skin color, specular reflectance of a nearly perpendicular beam from normal skin is always between 4–7% over the entire spectrum from 250–3000 nm. See R. Scheuplein, *J. Soc. Cosmet. Chem.*, v.15, pp. 111–122 (1964). Only the air-stratum corneum border gives rise to a regular reflection. Results from a previous study indicate that the indices of refraction of most soft tissue (skin, liver, heart, etc) lie within the 1.38–1.41 range with the exception of adipose tissue, which has a refractive index of approximately 1.46. See J. Parrish, R. Anderson, F. Urbach, D. Pitts, *UV-A: Biologic Effects of Ultraviolet Radiation with Emphasis on Human Responses to Longwave Ultraviolet*, New York, Plenum Press (1978). Therefore, these differences in refractive index between the different layers of the skin are too small to give a noticeable reflection. See Ebling, supra. The differences are expected to be even more insignificant when the stratum corneum is hydrated, owing to refractive index matching.

The 93–96% of the incident beam that enters the skin is attenuated due to absorption or scattering within any of the layers of the skin. These two processes taken together essentially determine the penetration of light into skin, as well as remittance of scattered light from the skin. Diffuse reflectance or remittance is defined as that fraction of incident optical radiation that is returned from a turbid sample. Absorption by the various skin constituents mentioned above account for the spectral extinction of the beam within each layer. Scattering is the only process by which the beam may be returned to contribute to the diffuse reflectance of the skin. Scattering results from differences in a medium's refractive index, corresponding to differences in the physical characteristics of the particles that make up the medium. The spatial distribution and intensity of scattered light depends upon the size and shape of the particles relative to the wavelength and upon the difference in refractive index between the medium and the constituent particles.

The scattering coefficient of biological tissue depends on many uncontrollable factors, which include the concentration of interstitial water, the density of structural fibers, and the shapes and sizes of cellular structures. Scattering by collagen fibers is of major importance in determining the penetration of optical radiation within the dermis. See F. Bolin, L. Preuss, R. Taylor, R. Ference, *Appl. Opt*, v. 28, pp. 2297–2303 (1989). The greater the diffusing power of a medium, the greater will be the absorption due to multiple internal reflections. Therefore, reflectance values measured on different sites on the same person, or from the same site on different people, can differ substantially even when the target absorber is present in the same concentration. These differences can be attributed to gender, age, genetics, disease, and exogenous factors due to lifestyle differences. For example, it is known that skin thickness in humans is greater in males than females, whereas the subcutaneous fat thickness is greater in females. The same group reports that collagen density, the packing of fibrils in the dermis, is higher in the forearms of males than females. See S Schuster, M. Black, E. McVitie, *Br. J. Dermatol*, v.93, pp.639–643, (1975).

Dynamic Properties of the Skin

While knowledge of and utilization of the optical properties of the skin, high instrument sensitivity and compensation for inherent nonlinearities are all vital for the application of near-infrared spectroscopy to noninvasive blood analyte measurement, an understanding of biological and chemical mechanisms that lead to time dependent changes in the optical properties of skin tissue is equally important and, yet, largely ignored. At a given measurement site, skin tissue is often assumed to be static except for changes in the target analyte and other absorbing species. However, variations in the physiological state of tissue profoundly affect the optical properties of tissue layers and compartments over a relatively short period of time.

Such variations are often dominated by fluid compartment equalization through water shifts and are related to hydration levels and changes in blood analyte levels.

Total body water accounts for over 60% of the weight of the average person and is distributed between two major compartments: the extracellular fluid (one-third of total body water) and the intracellular fluid (two-thirds of total body water) [see A. Guyton, J. Hall, *Textbook of Medical of Physiology*, $9^{th}$ ed., Philadelphia, W. B. Saunders Company (1996)]. The extracellular fluid in turn is divided into the interstitial fluid (extravascular) and the blood plasma (intravascular). Water permeable lipid membranes separate the compartments and water is transferred rapidly between them through the process of diffusion, in order to equalize the concentrations of water and other analytes across the membrane. The net water flux from one compartment to another constitutes the process of osmosis and the amount of pressure required to prevent osmosis is termed the osmotic pressure. Under static physiological conditions the fluid compartments are at equilibrium. However, during a net fluid gain or loss as a result of water intake or loss, all compartments gain or lose water proportionally and maintain a constant relative volume.

A mechanism for distributing substances contained in blood serum that are needed by the tissues, such as water and glucose, is through the process of diffusion. The invention recognizes that Fick's law of diffusion drives the short-term intra-/extra vascular fluid compartment balance. The movement of water and other analytes from intravascular to extravascular compartments occurs rapidly as tremendous numbers of molecules of water and other constituents, in constant thermal motion, diffuse back and forth through the capillary wall. On average, the rate at which water molecules diffuse through the capillary membrane is about eighty times greater than the rate at which the plasma itself flows linearly along the capillary. In the Fick's Law expression, the actual diffusion flux, $I_{OA}$, is proportional to the concentration gradient, $dc/dx$ between the two compartments and the diffusivity of the molecule, $D_A$ according to the equation $$I_{OA} = -D_A \left( \frac{dc}{dx} \right). \qquad (1)$$

Short-term increases (or decreases) in blood glucose concentrations lead to an increase (or decrease) in blood osmolality (number of molecules per unit mass of water). Fluid is rapidly re-distributed accordingly and results in a change in the water concentration of each body compartment. For example, the osmotic effect of hyperglycemia is a movement of extravascular water to the intravascular space. Conversely, a decrease in blood glucose concentration leads to a movement of water to extravascular space from the intravascular compartment.

Because the cell membrane is relatively impermeable to most solutes but highly permeable to water, whenever there is a higher concentration of a solute on one side of the cell membrane, water diffuses across the membrane toward the region of higher solute concentration. Large osmotic pressures can develop across the cell membrane with relatively small changes in the concentration of solutes in the extracellular fluid. As a result, relatively small changes in concentration of impermeable solutes in the extracellular fluid, such as glucose, can cause tremendous changes in cell volume.

Sampling Error

Noninvasive measurement of tissue properties and analytes, such as blood glucose concentration, may employ NIR spectroscopic methods. S. Malin, T. Ruchti, U.S. Pat. No. 6,280,381, supra, describes a system for noninvasively measuring blood glucose concentrations in vivo, using NIR spectral analysis. Such NIR spectroscopy-based methods utilize calibrations that are developed using repeated in vivo optical samples of the same tissue volume. These successive measurements must yield a substantially repeatable spectrum in order to produce a usable calibration. As herein described, the heterogeneous and dynamic nature of living human skin leads to sampling uncertainty in the in vivo measurement. As previously described, sampling differences can arise due to variable chemical composition and light scattering properties in tissue. As an example: because glucose is not uniformly distributed in tissue, a variation in the volume of tissue sampled is likely to lead to a variation in the strength of the glucose signal, even though glucose concentration in the tissue or blood remains constant. Variation in the repeated placement of the optical probe used for sampling at the measuring surface site can lead to sampling in errors in two separate ways: first, variations in location of the probe can cause a different tissue volume to be sampled, and second, varying the amount of pressure applied by the probe on the tissue can alter the optical scattering by the tissue, thereby changing the sampled tissue volume. A change in optical sampling may lead to a variation in the spectral signal for a target analyte even though the concentration of the analyte in the blood or tissue remains unchanged. Furthermore, air gaps between the surface of the optical probe and the surface of the tissue being sampled give rise to variable surface reflection. Variable surface reflection leads to a variable light launch into the tissue that in turn gives rise to an increase in the nonlinear nature of the spectral measurements. Certainly, a variable nonlinear measurement would be very difficult to calibrate.

Commercialization of Near-infrared Instrumentation

The noninvasive measurement of trace analytes, such as glucose, through near-infrared technology, requires a stable spectroscopic measurement system with a high signal-to-noise ratio (greater than 20,000-to-1 measured as the dynamic range divided by the RMS noise). Interference related to instrument malfunction or environmental influences on the instrumentation cause uncertainty in the affected measurements. Therefore, the development of a robust apparatus with the necessary performance characteristics is exceedingly challenging. In addition, a device that is suitable for use in clinics and the diverse environments experienced by the consumer must be durable, stable and robust despite environmental fluctuations and user misuse.

The Problem

The noninvasive measurement of glucose is challenging due to the complex structure of the sample, the presence of interfering analytes, the dynamic nature of tissue, the small signal related to glucose, physiological conditions interfering with the measurement and instrumental effects leading to uncertainty. Any one of the aforementioned effects has the potential under a variety of conditions of influencing the spectroscopic measurement and introducing error into the noninvasive determination of glucose. Various means for compensating for such variation have been reported. For example, T. Blank, G. Acosta, M. Mattu, M. Makarewicz, S. Monfre, A. Lorenz, T. Ruchti, Optical sampling interface system for in vivo measurement of tissue, U.S. patent application Ser. No. 10/170,921 (Jun. 12, 2002), describe a system for reducing variation related to surface effects, improving the uniformity of surface hydration and providing a precise sampling measurement. However, even with the development and use of compensations for reducing both the probability and magnitude of the effects related to measurement error, each source of measurement interference can cause an erroneous measurement under extreme or exaggerated circumstances. Furthermore, the potential for the occurrence of erroneous measurements has a profound and detrimental affect on the safety and efficacy of the medical application of noninvasive systems for measurement of glucose and without remediation severely limits the potential usage of this technology in therapeutic and diagnostic applications. Therefore, the presence of conditions leading to erroneous measurements must be detected through a comprehensive system that identifies conditions likely to lead to an erroneous measurement.

In view of the problems left unsolved by the prior art, there exists a need for a method and apparatus to detect conditions leading to erroneous noninvasive glucose measurements. Furthermore, it would be a significant advancement to provide a comprehensive error detection system capable of diagnosing the source and nature of the error.

SUMMARY OF THE INVENTION

The error detection system (EDS) operates on a near infrared measurement of in vivo skin tissue. The architecture employs a pattern classification engine and hierarchy of levels to analyze, detect and diagnose instrument, interface and sample errors manifested in the near-infrared measurement. A priori information about the sources of errors is used to establish preset limits and categories of errors. Application of the system results in improved prediction accuracy through the rejection of invalid and poor samples.

The invention involves a noninvasive near-infrared glucose meter, an error detection system (EDS), a system for diagnosing and mitigating errors and a reporting method (FIGS. 1–3). The meter is a near-infrared spectrometer that makes a near-infrared based measurement of the patient's skin tissue. The error detection system, shown in FIG. 6, performs a series of tests based upon an ordered hierarchy to determine the suitability of the near-infrared measurement for blood glucose measurement. The final component of the system evaluates the error condition, diagnoses the specific mode of failure (if necessary) and reports the actions to be taken (FIG. 8).

The system of the invention is organized into a hierarchy of levels that receive and inherit information from lower levels (FIG. 2). The lowest level is applied to the near-infrared measurements (or spectra) of all patients (i.e., it is not customized to the patient) on the basis of rudimentary specifications required for acceptable noninvasive blood glucose measurement. The mid-level utilizes patient history information to perform a more detailed examination of the data for errors and the upper-level uses the calibration database to assess the acceptability of the data for glucose measurement.

Errors generated by each level are inherited by succeeding (higher) levels for error diagnosis until a critical error is encountered (one that prohibits further analysis). The generated error leads to various actions for mitigating the problem from simple sample rejections to patient re-calibration. As illustrated in FIG. 2, the level of the error dictates the highest level of prescribed action.

The system is composed of a multiplicity of elements, each involved in an aspect of the system of error detection. Each sub-component involves a test to determine whether or not an error condition has occurred on the basis of a calculated variable and a statistically based or empirically determined range of acceptability. A distinguishing quality of the sub-components is that they were derived from the a priori knowledge of the optical properties of tissue, the basis of spectroscopic measurement and calibration, tissue physiology, the effect of structural deformity of the tissue sample, and the necessary requirements for the non-invasive measurement of glucose. Therefore, the majority of the error conditions also provide useful information for diagnosing the source of the error. The composite of the sub-component outcomes serves as an input for a knowledge base system used to diagnose the specific source of error. Finally, with the source of error diagnosed, a database is used to provide corrective instructions.

In addition, each sub-component and each level of the error detection system is capable of operating independently of the other levels and sub-components to the benefit of a noninvasive glucose measurement system (see FIG. 3). For example, in FIG. 6, the low-level subsystem is useful apart from the more sophisticated levels in detecting instrumental malfunctions and gross sampling errors and, as shown in FIG. 3C, can be applied in a manner that is independent of the other levels. Similarly, the mid and high-levels can be used apart from the other levels. Alternately, each individual element of FIG. 8 can be used as a method for error detection apart from the other elements. Therefore, the invention alternately provides a system, sub-systems (levels) and individual processes for detecting errors during noninvasive glucose measurement.

DETAILED DESCRIPTION

Figure 4:
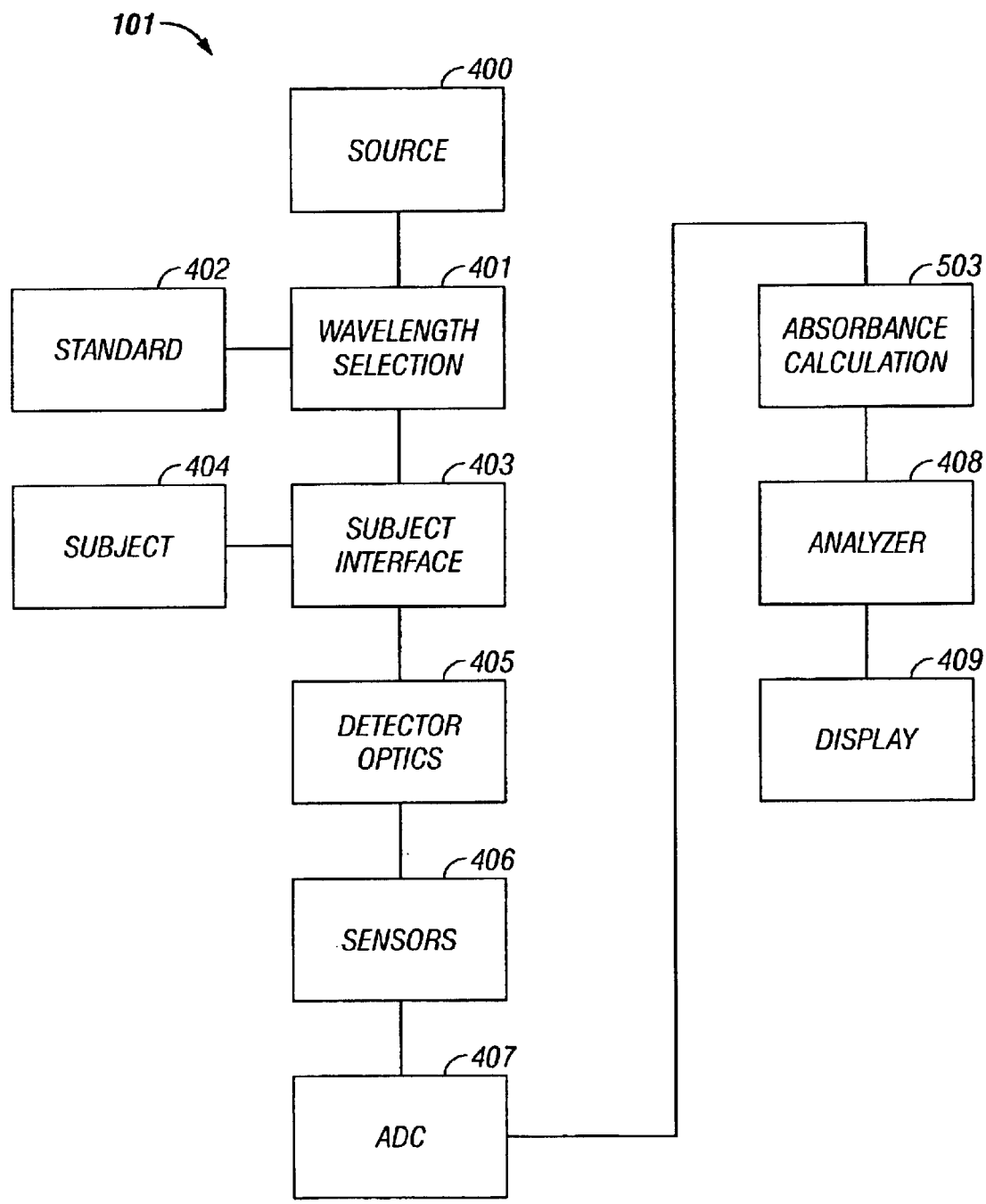
FIG. 4 shows a block diagram of a spectroscopic measurement system according to the invention.
Figure 5:
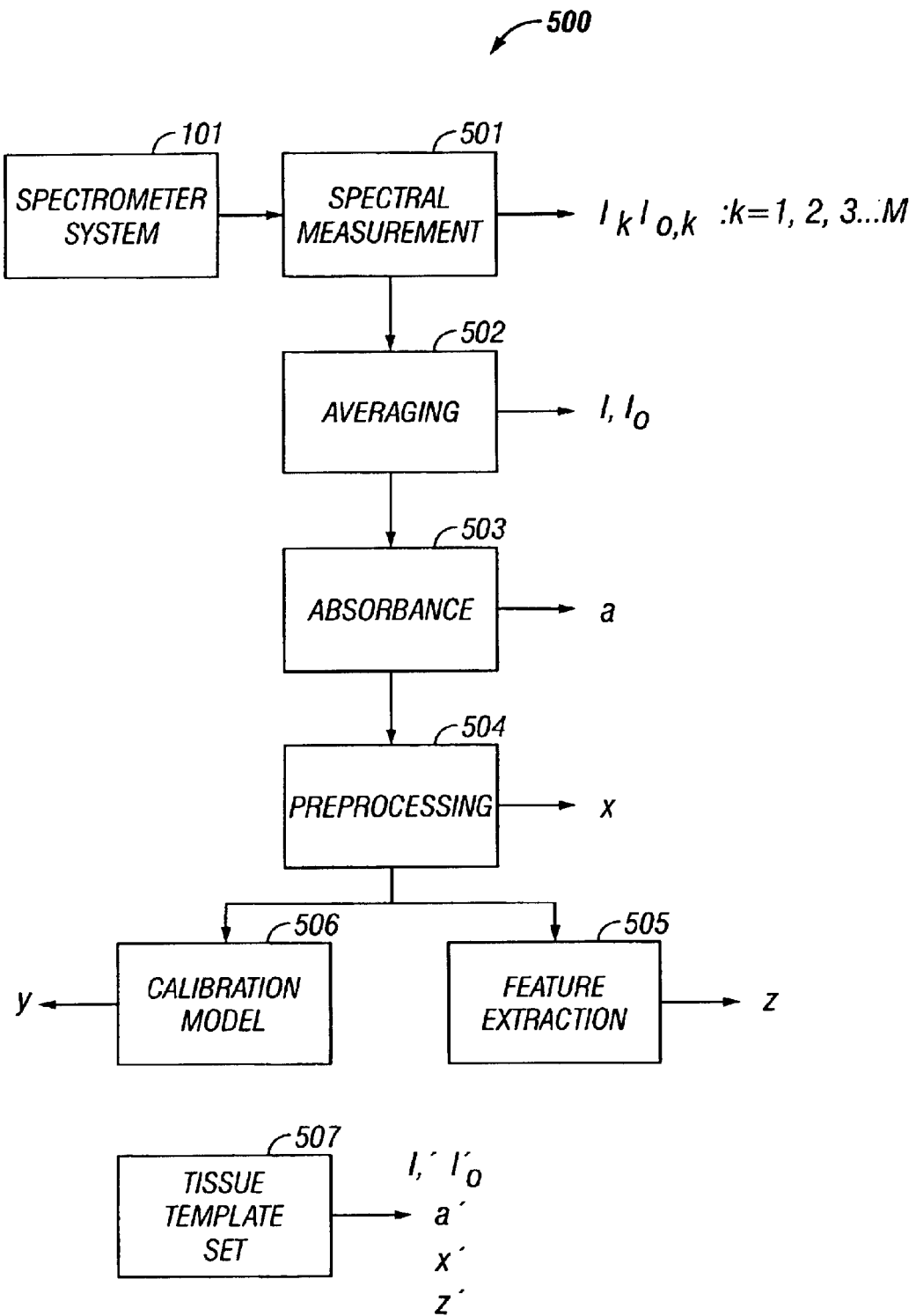
FIG. 5 provides a block diagram of a preprocessing and feature extraction system according to the invention.
Figure 8:
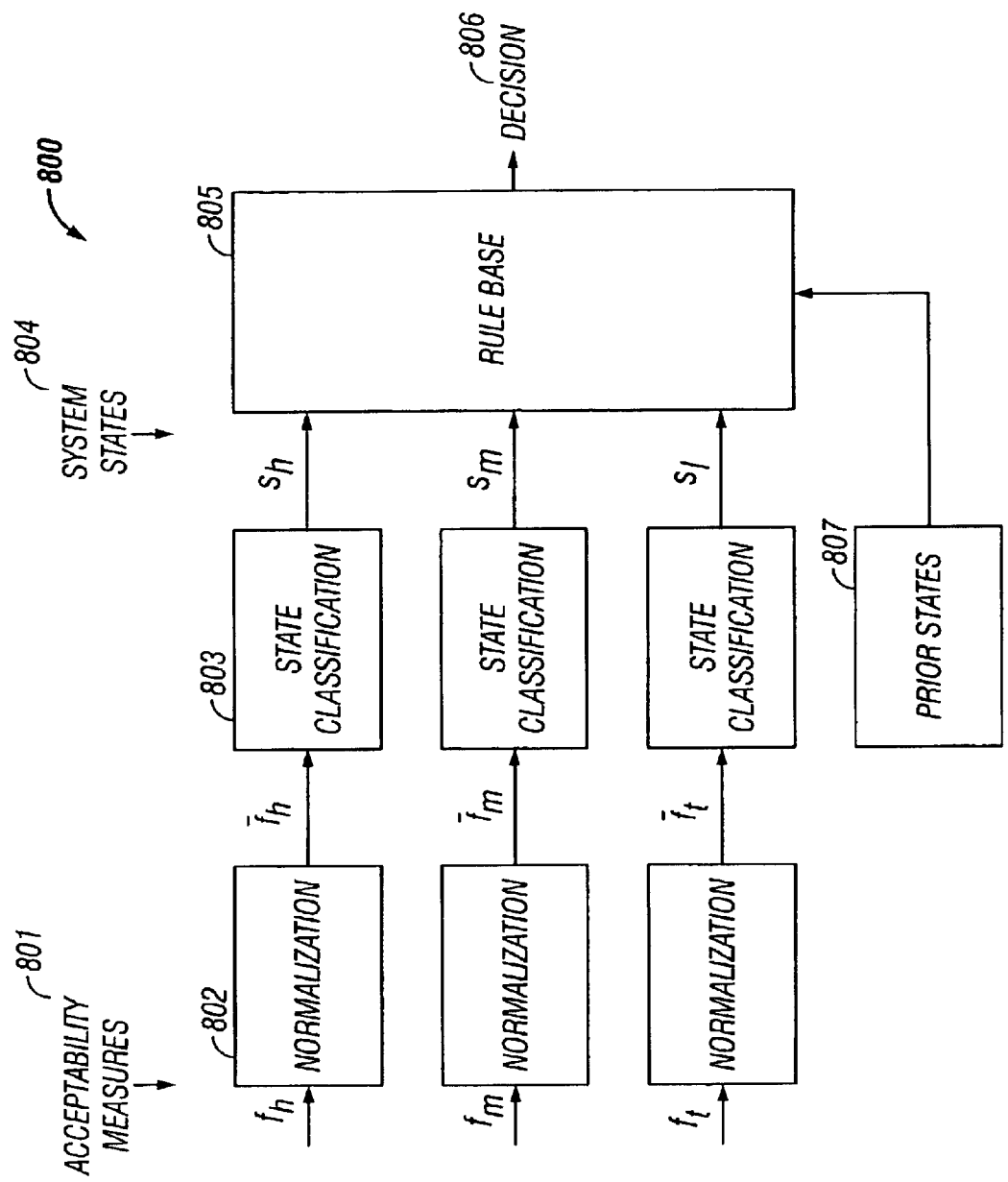
FIG. 8 provides a block diagram of a state classification and rule-based decision system from the system of FIG. 1 according to the invention.

The invention provides a system 100 and method for detecting errors in the spectroscopic measurement of glucose through the following components:

spectroscopic measurement apparatus (FIG. 4)

preprocessing and feature extraction system (FIG. 5)

an error detection system (FIG. 6) involving any of:
  individual processes and methods for detecting errors;
  sub-systems comprised of processes and methods having commonality, such as the level of sophistication, for detecting errors;
  A hierarchal system constituting one or more levels for detecting errors; and pattern classification system and decision engine (FIG. 8).

The spectroscopic measurement system determines the near-infrared intensity and absorbance of a particular tissue sample site. The measured data is provided to the processing and feature extraction system for the extraction of features, determination of absorbance and processing. These steps are performed to enhance particular aspects of the data indicative of error conditions and for the enhancement of the analytical signal related to glucose. The hierarchical error detection system employs levels of sophistication for developing a set of acceptability measures and detecting errors. The acceptability measures are used in conjunction with state classification and a decision engine to provide a systems level means of detecting conditions unsuitable for glucose measurement and diagnosing the source of the problem.

Spectrometer Measurement Apparatus

The Intelligent Error Detection and Diagnosis System is implemented in a spectroscopic system that determines the NIR intensity and absorbance spectrum of a tissue site through a diffuse reflectance measurement.

Referring to FIG. 4, The spectroscopic measurement system 101 consists of a source of near-infrared radiation 400, a wavelength selection system 401, an interface to the patient, a means for directing the near-infrared radiation to the skin 403 and a means for directing radiation reflected or transmitted from the skin 205, a means for detecting near-infrared radiation that is reflected or transmitted from the skin 406, a means for analyzing the detected near-infrared radiation 408 and a means for displaying the measured analyte, property or constituent 409 or alternately a means for displaying an error and related information. In an alternate arrangement, the wavelength selection 401 can occur between the subject interface 403 and the detector optics 405.

The source 400 radiates near-infrared energy in the wavelength range 700–2500 nm and may consist of, for example, an array of LED's or a halogen lamp. One or more bandpass filters may be provided to minimize the effect of wavelengths from outside of the spectral range of interest, but which are still emitted by the near-infrared energy source. For example, halogen lamps, while having peak energy at approximately 1600 nm, still give off electromagnetic radiation above 2500 nm. This has detrimental effects on the detection of glucose since wavelengths above 2500 nm have deleterious effects at the measurement site due to heating of the tissue and its respective components.

The method of wavelength separation 401, either before or after illumination of the skin, can be performed through the use of a dispersive element (e.g., a plane or concave, ruled or holographic grating), an interferometer, or successive illumination of the elements of an LED array without an additional dispersive element. Due to changes in performance of these wavelength separation methods caused by changes in the environment, it may be necessary to correct for these changes by scanning a reference wavelength standard 402, for example a polystyrene standard, either immediately before or after the interrogation of the tissue. In interferometer-based systems, this is done simultaneously with the interrogation of the tissue.

The sensing element(s) 406 are detectors that are responsive to the targeted wavelengths and may constitute either an array or a single element. In the case of linear diode arrays (or photodiode arrays), when two or more different detector materials are required to cover the wavelength region of interest, it is preferable that the material junction(s) occurs at a wavelength not required for the measurement. For example, in the case of InGaAs and extended InGaAs detectors, the junction typically occurs at 1750 nm for the purpose of reducing the cost of the array due to the high cost of extended InGaAs. However, this wavelength region occurs in the middle of the absorptions associated with fat, protein and glucose; thus, it is much preferable for the junction to occur at approximately 1480 nm±20 nm. In addition, it is preferable that the electronics used to sense the individual elements of the array have their junction occurring at the same wavelength.

The tissue sample interface includes a subject 404 interface module 403 by which near-infrared radiation is directed to and from 405 the tissue, either directly or through a light pipe, fiber optics, a lens system or a light directing mirror system. The area of the tissue surface to be irradiated and the area from which the returning near-infrared radiation is detected are different, being separated by a defined distance and selected in order to target a tissue volume optimal to measurement of the property of interest. The specularly reflected radiation from the irradiated site is of such a magnitude that it would greatly interfere with detection of the returned radiation. Thus, in offsetting the detection site from the irradiation site by a predetermined amount, it is possible to sample a volume of tissue that is a subset of the manifold of tissue that has affected the light that is being detected, while avoiding interference from specularly reflected light. In the case of a larger, tabletop or desktop instrument, the patient interface module further may include an elbow rest, a wrist rest, and a guide to assist in interfacing the illumination mechanism of choice and the tissue of interest. In the case of a smaller handheld unit, the patient interface module includes a guide or positioning mechanism to assist in interfacing the tissue of interest. Generally, as described above, an optical coupling fluid is placed between the illumination mechanism and the tissue of interest to minimize specular reflectance from the surface of the skin. Portions of the aforementioned patient interface module are described in U.S. patent application Ser. No. 09/563,782 and PCT Application No. US01/29232, the contents of both of which are hereby incorporated by reference in their entirety.

The collected near-infrared radiation is converted to a voltage and sampled through an analog-to-digital 407 converter for analysis on a microprocessor-based system 408 and the result of such analysis displayed 409.

The sample site, the surface or point on the subject the measurement probe comes into contact with, includes the specific tissue irradiated by the spectrometer system. The ideal qualities of the sample site include homogeneity, immutability, and accessibility to the target analyte. While several measurement sites can be used, including the abdomen, thigh, hand (palm or back of the hand), ear lobe, or finger; in the preferred embodiment, the volar part of the forearm is used. In addition, while the measurement can be made in transflectance, diffuse reflectance or diffuse transmittance mode, the preferred method is diffuse reflectance. The scanning of the tissue can be done continuously, in the case of an area not subject to pulsation effects, or the scanning can be done intermittently between pulses.

The instrument collects near-infrared measurements of a patient's tissue through a series of rapid scans. In addition, several reference spectra are collected using reflectance standards for instrument diagnostics and calculation of absorbance. The software system of the instrument includes a time history database for each patient and a calibration database that is accessible by the error detection system.

At the beginning of each day, a tissue template set (processed near-infrared measurement and related features) is collected on each patient along with pertinent information such as skin temperature, instrument state and environmental temperature.

Processing

The application of the error detection system occurs throughout the operation of the measurement system and at each stage of data collection. The data collection process occurs in several phases involving the collection of a reference spectrum as described previously and a tissue near-infrared measurement (a spectrum). Several processing steps, summarized in FIG. 5 are performed and each results in data used at various stages within the error detection system. These include:

Spectral Measurement 501, including;
    Averaging 502 (Ensemble averaging of multiple spectra)
    Absorbance 503 (Estimation of absorbance)
Preprocessing 504;
Feature Extraction 505; and
Assembly of the tissue template set 507.

Figure 6:
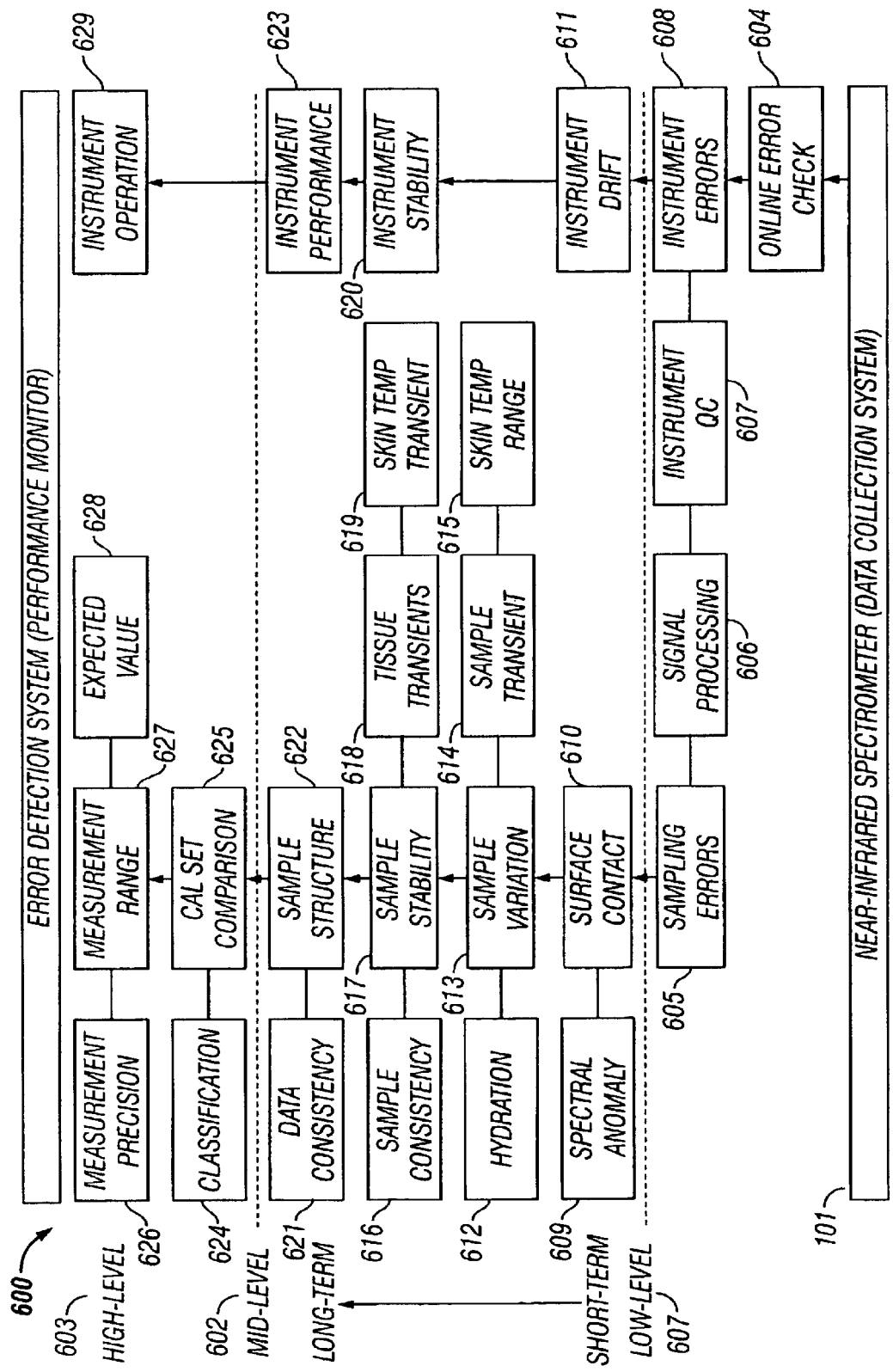
FIG. 6 provides a block diagram of an error detection system from the system of FIG. 1 according to the invention.

In addition, the calibration model 506 of the measurement system is employed for higher-level portions of the error detection system, as shown in FIG. 6. These items are described in the following sections prior to the description of the error detection system.

Preprocessing and Feature Extraction

The preprocessing and feature extraction system 500, shown in FIG. 5, implements methods for processing the spectral intensity measurements 502, calculating absorbance 503, preprocessing 504, feature extraction 505, estimation of glucose on the basis of a calibration 506 and determination of a tissue template set 507.

Processing

Figure 9:
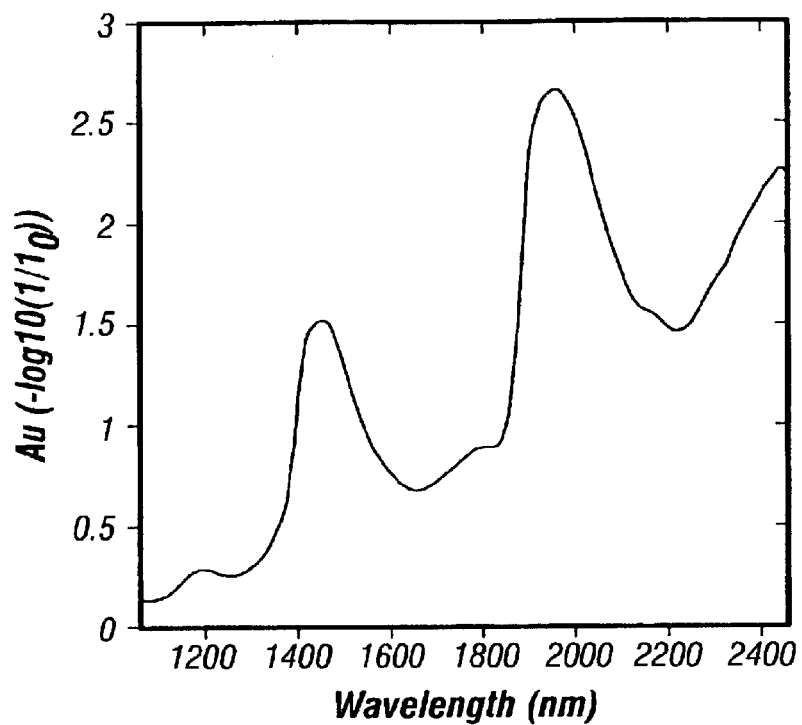
FIG. 9 shows a typical absorbance spectrum measured on the forearm of a human subject.

In the preferred embodiment, the measurement process 501 and absorbance calculation 503 is as follows: the measured intensity of light from the tissue, $I \in \Re^{M \times N}$, and the light intensity measured from a non-absorbing, uniformly absorbing or minimally absorbing reference material, $I_o \in \Re^{M \times N}$, each contain intensity levels pertaining to a set of N wavelengths, $\lambda \in \Re^N$, that are within the near-infrared portion (700–2500 nm) of the spectrum at M instants in time. Typically, the intensity is given in units of volts and low-level processing steps, such as the subtraction of an electrical offset from each raw intensity spectrum, occurs before the designation of an intensity spectrum. Both $I_o$ and I are averaged 502 across the wavelength range either through a simple average calculation or a robust estimate of the mean intensity at each wavelength. Absorbance 503 is determined according to $$a = -\log_{10}\left(\frac{I}{I_o}\right) \quad (2)$$

where a is the reflectance spectrum of the skin and is analogous to an absorbance spectrum containing quantitative information that is based on the known interaction of the incident light with components of the body tissue. A plot of a typical spectrum of a versus λ is shown in FIG. 9 and consists of absorption bands primarily due to water, fat, and protein. More particularly, however, the measurement can consist of a specific set of wavelengths in the near infrared region that have been optimized for the extraction of features and for the measurement requirements. For example, the measurement of glucose is optimally performed in the wavelength range 1100–1935 nm, or a selected subset thereof.

Alternatively, the spectral measurement can be determined according to $$a = -\log_{10}\left(\frac{I}{I_r}\right) \quad (3)$$

where $I_r \in \Re^{1 \times N}$ is a representation of the measured tissue intensity at some point in time prior to collection of I and can be determined from a single tissue intensity spectrum or from the mean or a robust estimate of the mean (e.g., the trimmed mean) of several tissue intensity spectra. In another embodiment, the measurement a, can be defined as the measured intensity, I, commonly referred to as a "single-beam spectrum". Finally, a may consist of either a single spectrum collected with an instrument or a combination of several (optimally) selected spectra collected over a defined measurement period and averaged. Methods for selecting the spectra, used to produce the lowest noise measurement, include similarity or distance measures (i.e., select the most similar) and clustering operations.

Further processing of the absorbance spectrum, a, is performed to enhance specific properties. Preprocessing 504 includes operations such as scaling, normalization, smoothing, derivatives, filtering and other transformations that attenuate the noise and instrumental variation without unduly affecting the signal of interest. The preprocessed measurement, $x \in \Re^N$, is determined according to $$x = h(\lambda, a) \quad (4)$$

where $h: \Re^{2 \times N} \to \Re^N$ is the preprocessing function and λ is the wavelength.

Feature Extraction

Feature extraction 505 is any mathematical transformation that enhances a quality or aspect of the sample measurement for interpretation [R. Duda, P. Hart, *Pattern Classification and Scene Analysis,* John Wiley and Sons, New York (1973)]. The general purpose of feature extraction is to concisely represent or enhance the chemical concentration, structural properties, and physiological state of the tissue measurement site. In the invention, a set of features is developed that represents or reflects the optical properties of the tissue based on:

- identification of distinct absorption bands that change in various ways with respect to changes in pathlength; and
- the scattering and absorption properties (or coefficients) of the measurement site.

Subsequently, the features are then applied to identify conditions unsuitable for glucose measurement. For example, a resolved estimate of the magnitude of the fat band absorbance can be used to infer specific information about the dermis. Since -fat is present in very low concentrations in the dermis, near infrared radiation must propagate through the dermis to penetrate into the adipose tissue beneath. Thus, physiological changes, and the corresponding changes in the optical properties of the dermis, influence the magnitude of the fat band absorbance.

Given the spectral measurement, a, or a spectral measurement pre-processed 504 by means of a filtering operation, first or second derivative calculation [A. Savitzky, M. Golay, *Smoothing and Differentiation of Data by Simplified Least Squares Procedures,* Anal. Chem., 36: 8, pp.1627–1639 (1964)] or scatter correction:

- "simple" features are the values of the spectral measurement or the processed spectral measurement at the critical points (the points at which the slope is zero);
- additional (derived) features are determined from the simple features through mathematical transformation such as addition, subtraction, division and multiplication; and
- abstract features are developed through linear and non-linear transformations of the pre-processed spectrum.

While simple and derived features generally have a physical interpretation, such as the magnitude of the fat absorbance, the set of abstract features do not necessarily have a specific interpretation related to the physical system. For example, the scores of a principal component analysis are used as features although their physical interpretation is not always known. The utility of the principal component analysis is related to the nature of the tissue absorbance spectrum. The most significant variation in the tissue spectral absorbance is not caused by the absorption of glucose but is related to the state, structure and composition of the measurement site. This variation is modeled by the primary principal components. Therefore, the leading principal components tend to represent variation related to the structural properties and physiological state of the tissue measurement site and consequently reflect the optical properties of tissue.

Figure 10:
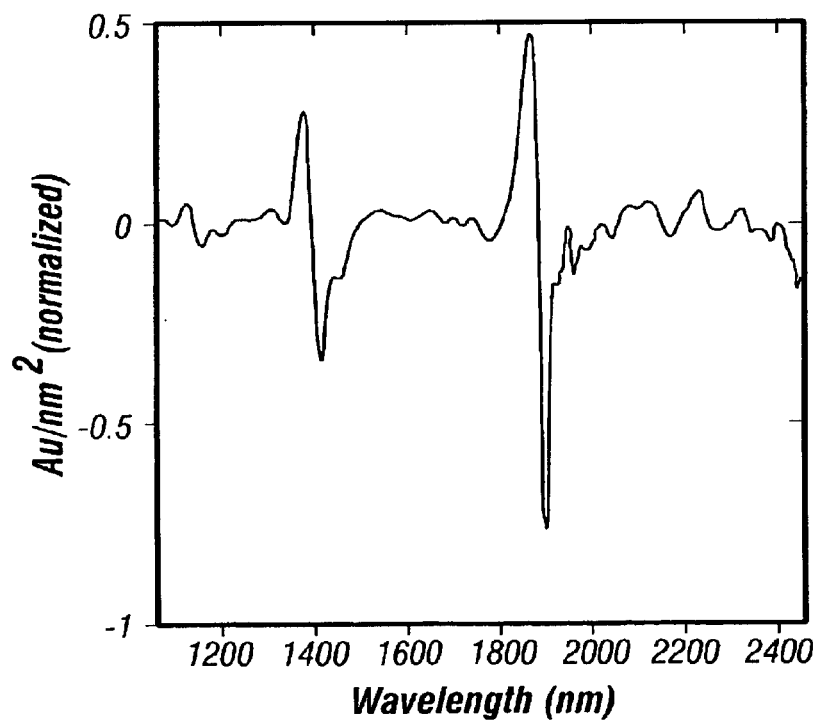
FIG. 10 shows a plot of the normalized second derivative of an absorbance spectrum versus wavelength.

In the preferred embodiment, the features are determined from the second derivative of the absorbance spectrum shown in FIG. 10. Each critical point is identified according to its wavelength. The value of the second derivative spectrum at each critical point is used as a feature to represent a key property of the tissue sample associated with the measurement spectrum. In FIGS. 11 through 16, many key features are identified as exemplary measurements. These include:

Normalization points (n) 1–8 near 1665, 1708, 1746, 1868, 1380, 1133, 2020, and 2232 nm respectively;

Fat bands points (f) 1–4 near 1727, 1765, 1214, and 1165 nm;

Protein band points (p) 1–9 near 1687, 1715, 1190, 2050, 2150, 2175, 2275, 2292, and 2355 nm; and Water band points (w) 2–6 near 1789, 1896, 1410, 1465, and 1150 nm.

Normalization points, n1–n8, are generally used to determine derived features and points designated as "fat" (f1–f4), "protein" p1–p9 and "water" w2–w6 are generally located in the vicinity of an absorption band due to fat, protein, or water respectively. Due to the bandwidth (lower resolution) of the second derivative spectrum, several of the bands associated with one constituent include absorbance due to another and a few of the critical points are associated with a constituent, because their location is in the vicinity of the respective constituent. In addition, the wavelengths are reported for the features shown in the example second derivative spectrum (FIG. 10) and can change substantially as a result of variation in the reduced scattering coefficient and the inner filter effect related to the multiple layers of the skin.

Additional features have been derived and are noted on the plots. For example, $d1=n_{1665}-p_{1687}$, $d2=n_{1665}-f_{1727}$, $d3=n_{1665}-f_{1765}$, $d4=n_{1665}-w_{1789}$, $d5=n_{1868}-w_{1410}$, $d6=n_{1380}-w_{1465}$ and $d7=n_{1380}-w_{1150}$, where the notation $p_\lambda$, $w_\lambda$, $f_\lambda$, and $n_\lambda$, designate the protein, water, fat, or normalization points designated previously that are close to the wavelength $\lambda$. Additional derived features that are used for error detection and measurement include d2/d1.

While specific examples of features have been provided in this context, one skilled in the art will recognize that many useful features have not been listed that can be derived from any of the absorbance spectrum, the first derivative spectrum or a preprocessed absorbance spectrum. Additionally, a principal components analysis provides additional abstract features that are useful for tissue transient identification, outlier analysis, and analyte measurement. In certain instances, the entire spectrum, after suitable preprocessing, is passed to the measurement module in which a calibration is applied to estimate or predict the concentration of blood glucose.

Tissue Template Set

A tissue template set 507 is collected at the onset of a measurement period. Generally, the measurement period is defined as the period of time over which the combined tissue sample and instrument are consistent. As shown in FIG. 5, the tissue template set consists of the reference spectrum, $I_o$; the tissue intensity spectrum, I; the arm absorbance spectrum, a; the processed tissue absorbance spectrum, x; and the set of extracted features, z. The collection procedure for the tissue template involves the collection of P tissue replicates, each containing M reference and tissue spectra. Each spectra is ensemble-averaged by wavelength to produce a set of P averaged tissue replicates. The tissue replicates are then averaged using a robust estimate (for example, 50% trimmed mean) at each wavelength.

Calibration and Measurement

Previously we reported methods for calibration and measurement of tissue analytes [see Malin, et al. supra and T. Ruchti, S. Thennadil, T. Blank, A. Lorenz, S. Monfre, Noninvasive measurement of glucose through the optical properties of tissue, PCT Application No. US02/02288, filed on Jan. 25, 2002]. For the purpose of outlier and error detection, a calibration model 506 is utilized to estimate the relative precision of the measurement, and, at times, to determine the certainty of a particular measurement in view of past measurements. As described in Malin, et al. and Ruchti, et al., both supra, the measurement of an analyte is accomplished through the application of a calibration model to the processed tissue measurement and/or the extracted features. The model is determined from a calibration set of exemplary paired data points each consisting of a preprocessed tissue measurement (x) and an associated reference analyte value (y) determined from an analysis of a blood or interstitial fluid sample. According to this process, blood, serum, plasma, or interstitial draws are taken from a tissue site that is either near the sensor sample site or has been designed/determined to reflect the sample site. For example, when non-invasive near-infrared measurements for the purpose of glucose measurement are taken for calibration on the forearm, it is possible in some individuals to collect a capillary blood draw from the same forearm or an alternate site such as opposite forearm. Alternately, rather than using blood draws, it is beneficial in some instances to use interstitial glucose values rather than capillary glucose values.

The calibration set is based on one or more subjects and generally contains glucose concentrations that represent the expected range of glucose variation and that include spectral variation representative of that likely to be encountered in future spectral measurements. The calibration model includes an equation, a set of parameters and corresponding computer code that is implemented to measure the subject's glucose level on the basis of the preprocessed spectral measurement.

In the preferred embodiment of the invention, the spectral measurement, a, is preprocessed and is followed by wavelength selection to create the preprocessed vector, x. The preprocessed spectrum is corrected to the tissue template and a multivariate method, such as partial-least squares regression, is applied to develop the calibration model. Glucose is then measured through the application of the identical preprocessing steps to a tissue measurement (preprocessing and tissue template correction) to obtain the processed spectral measurement, x. The glucose measurement associated with the spectral measurement is determined according to $$\hat{y} = xG + b \qquad (5)$$

where $G \in \Re^{N \times 1}$ is a linear transformation, derived from partial least-squares regression that represents both the feature extraction step and the calibration model.

Error Detection System

Figure 1:
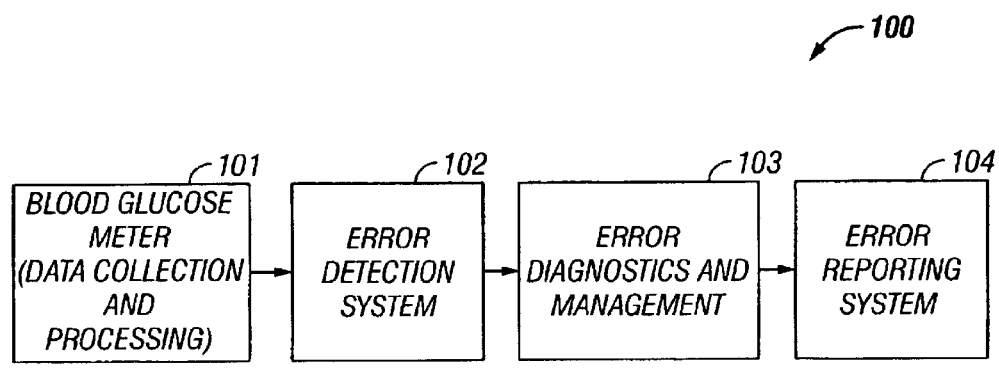
FIG. 1 provides a block diagram of an intelligent error detection system according to the invention.
Figure 2:
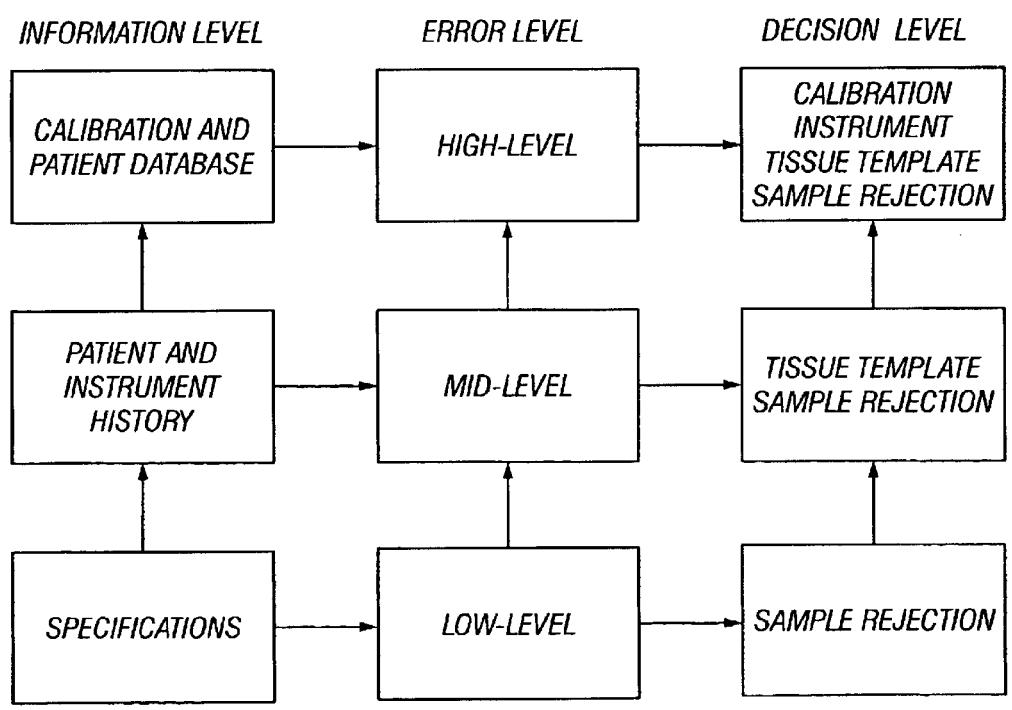
FIG. 2 provides an information, error, and decision flow diagram for the system of FIG. 1 according to the invention.

The error detection system 600, shown in FIG. 6, performs tests on the reference and patient spectra to determine the suitability of the collected data for making a noninvasive glucose measurement. As described above, the tests are performed through various levels. The level distinctions are based on the nature of information used for the test and the level of action taken as a result (see FIG. 2).

Low-level 601 tests are performed on the basis of measurement specifications common to all instruments and all patients. The potential actions taken include sample rejection and instrument QC check.

The mid-level 602 tests utilize patient and instrument history information in the form of a database in addition to the measurement specifications. The possible actions include instrument maintenance, and re-collection of the patient's tissue template set in addition to the low-level actions.

The high-level 603 system inherits the information from the lower levels and uses the calibration database to inspect the near-infrared scans. Additional actions taken by the high-level module include: change the calibration model; re-calibrate the patient; instrument failure; and invalid glucose measurement.

As described previously, each process, sub-system, and level can be employed independently of the other elements for the detection or errors. However, the combination of the elements and levels in the form of a hierarchical system provides additional benefits that result from the multiplicity and diversity of the individual tests.

An error manager coordinates the entire system by keeping a record of errors. When repeated errors occur at a particular level within the system, the level of response is increased due to the improved confidence in diagnosing an error from multiple replicates. For example, rudimentary low-level errors may initially lead to the re-collection of a particular spectrum. However, a repeated error may cause the re-collection of a sample and lead ultimately to an instrument malfunction error.

In each error test, listed as a sub-component of a particular level, a measure of acceptability, f, is developed. Each sub-component has a defined range of acceptability for its associated measure of acceptability. The range of acceptability for each method is determined empirically through a set of exemplary samples exhibiting both erroneous measurements of known origin and "good" samples.

Errors are generated by individual sub-components on the basis of these specific tests. In addition, during error-free operation the acceptability measures of each level are provided to the state classification and rule based system 800 shown in FIG. 8 for further evaluation.

Low-level Errors

Low-level error checks 601 are performed on data collected on all patients and involve the most rudimentary tests for data acceptability. These tests occur during and immediately after the collection of the reference spectra and the tissue spectra. The tests for acceptability are derived from specifications for non-invasive glucose measurement, a priori knowledge, and empirical data sets. If a deviation from the specified level of acceptability is detected, the resulting action is the rejection of the collected spectrum, the rejection of the entire sample or the generation of an instrument malfunction error.

The data provided to the low-level subsystem by the system manager includes instrument performance specification and target spectra for each type of material that is scanned by the system. The specifications include, for example, noise limits, minimum, operating temperature limits, and maximum signal levels and wavelength accuracy and precision limits.

Online Error (Real-Time) Check

Online Error Check 604 determines whether the proper material has been scanned and whether the material characteristics are similar to previously set standards during collection of the reference and patient spectra associated with a sample. For example, during normal operation the user is prompted by the software system to place the tissue measurement site on the patient interface module. If the user were to place something other than the target tissue sample site on the patient interface module, the Online Error Check Sub-Module would generate a method indicating an incorrect material had been placed or a continued prompt for the desired material would occur.

Figure 7A:
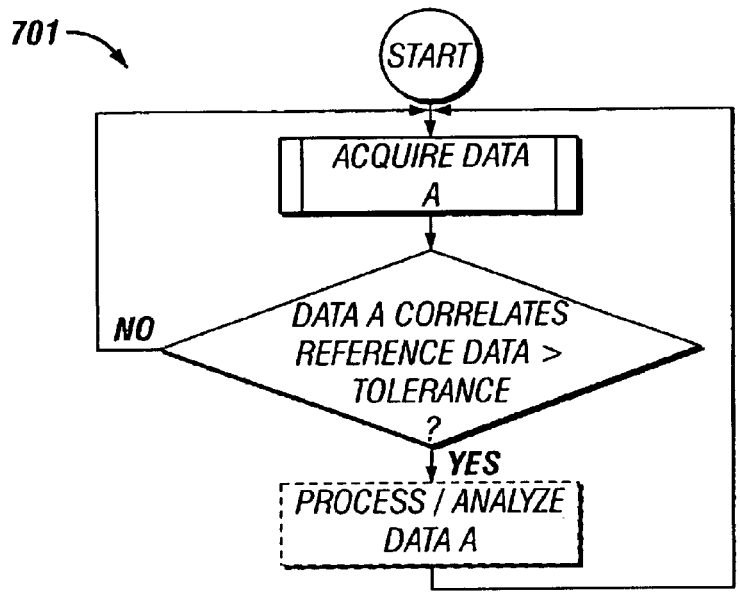
FIG. 7 shows a pair of decision flow diagrams from the error detection system of FIG. 6 according to the invention.

Anomalous spectral scans are detected by comparing the collected spectra, I or $I_o$, to the target spectra through a simple pattern matching step that includes but is not limited to cross-correlation, correlation coefficient, coefficient of determination, Root Mean Squared (RMS) difference, and linear and non-linear combinations of the spectrum at a single or a set of carefully selected wavelengths to yield a unique value related to the specific material being scanned. In the preferred embodiment, shown in FIG. 7A, the correlation between the new sample spectrum ('Data A' in FIG. 7A) and the target spectrum ('Reference Data') of the same material is computed. Each spectrum is optionally processed to reduce noise, especially when the test is performed on spectra that have not been averaged. Samples having a correlation less than a preset limit (Tolerance0 are rejected 701. In this embodiment $$f_{t,1} = 1 - corrcoef(I, I_{target}) \qquad (6)$$

where I is the measured intensity spectrum, $I_{target}$ is the target intensity spectrum and corrcoef( ) refers to the correlation coefficient operation. An error is generated if f>0.1.

In an alternate embodiment, a set of wavelengths is used that discriminate between the material types. The intensity at each wavelength is compared to a target through a distance measure, such as the Euclidean distance, to yield an estimate of the acceptability.

Figure 7B:
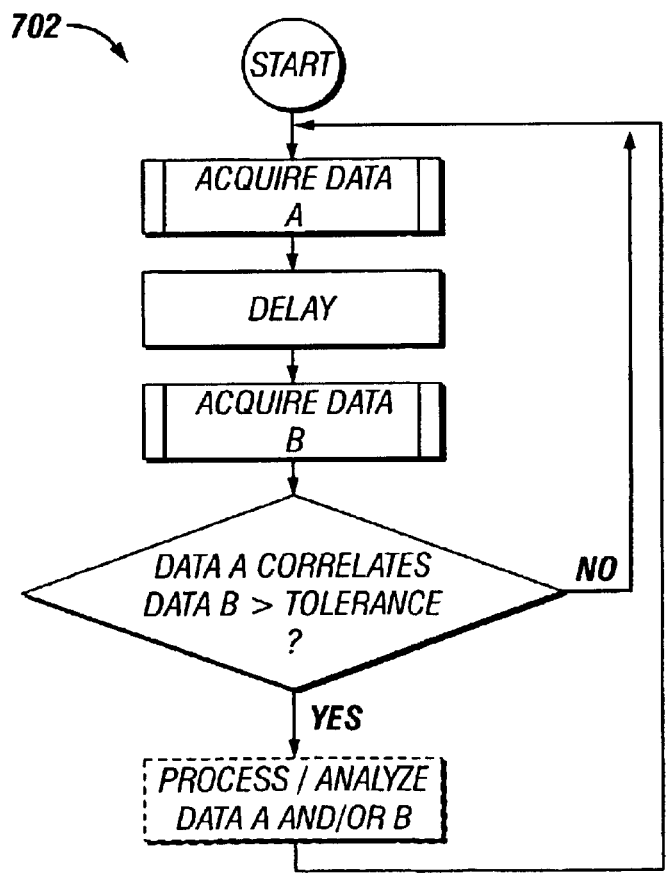

Another method (FIG. 7B) for material checking is the comparison of successive intensity spectra ('Data A,' 'Data B') through a simple pattern-matching step. In the preferred embodiment, the correlation between successive sample spectra is computed. The sample material is only scanned when the correlation exceeds a target value 702.

In any embodiment, the material check is performed in a nearly continuous manner immediately after the collection of intensity spectra. The results of the check are used by the software system to determine when a particular sample is coupled to the instrument and ready for further scanning. This prevents the scanning of an inappropriate material and enables the instrument to determine exactly when the user has placed either a reference or a tissue sample on the device. Thus, when an incorrect material is detected, the system simply waits for the correct material to be put in place.

Instrument Errors

Instrument related errors 608 are detected through the application of a set of requirements accentuating gross problems. These include, for example, illumination system failure, excessive instrument temperature, cracked or broken illumination/detection fibers, and excessive changes in light intensity indicating malfunction. Instrument errors are therefore detected on the basis of a series of tests that evaluate the signal levels compared to a target range of particular wavelengths that is indicative of each mode of failure.

Given a particular category of instrument error related to the optical system, the acceptability measures are defined as the difference between a target intensity at one or more wavelengths or wavelength regions and a target intensity according a distance measure. For example, given the target intensities, $I_{T,\lambda}$, at n wavelengths the following measure of acceptability is defined $$f_{t,2} = \sqrt{\frac{1}{n}\sum_{\lambda}(I_\lambda - I_{T,\lambda})^2} \ . \qquad (7)$$

For temperature related failures, the target intensities are replaced by a target temperature and the acceptability measure is defined as the distance from the target.

Instrument QC

The Instrument QC tests 607 determine if the instrument is operating according to instrument specifications. Instrument noise, signal-to-noise ratios, signal strength, and operating temperatures are measured and compared to preset specifications. If the instrument is not operating according to specifications, an error will be displayed on the computer system of the device.

The tests performed in the QC module are related directly to the instrument specifications necessary for measurement of glucose non-invasively. These include the following: instrument noise (at each wavelength and overall), peak signal level and x-axis variation. Given, for example, an estimate of the noise, $n_\lambda$, at each wavelength, $\lambda$, calculated by the root mean square intensity at each wavelength of the M reference intensity spectra, the acceptability measure is calculated according to $$f_{I,3}=\|n\| \tag{8}$$

where $\|\cdot\|$ is the norm. When $f_{I,3}$ exceeds a preset noise level corresponding to $\frac{1}{20,000}$ of the dynamic range of the measurement system, an error is generated.

The peak intensity of the reference spectra is compared to a target value through $$f_{I,4}=|\max(I_o)-I_{o,T}| \tag{9}$$

where $I_{o,T}$ is the target maximum intensity. When $f_{I,4}$ exceeds $\frac{1}{20}$ of the dynamic range of the instrument an error is generated. Similarly, measures of acceptability are provided for each of the QC tests referred to previously.

Signal Processing

This Signal Processing module 606 processes all scanned materials into a set of spectra that can be used to perform error detection and measure blood glucose. As described earlier, these include baseline correction, ensemble averaging, wavelength standardization, Finite Impulse Response (FIR) filtering, differentiation, multiplicative scatter correction (MSC), standard normal variate (SNV) transformation, and absorbance conversion are employed in the signal processing system.

Sampling Error

The sampling error module 605 detects gross sampling errors. Lifting/moving the arm during a scan, moving a reference during a scan, and improper coupling fluid application are just a few examples of gross sampling errors.

In the case of reference spectra, the method is applied to reject replicate spectra that are corrupted by noise or other sources of variation. In the preferred embodiment, reference spectra are mean-centered and inspected for spectral data points that have an absolute value above a predetermined limit at a particular wavelength. Spectral scans that have any data points exceeding a preset absolute limit will be removed. If the total number of scans removed from a particular sample exceeds a predetermined limit, an error message is indicated.

In the case of the arm sample, 'sampling errors' error detection is based on knowledge of the minimum absorbance of a properly coupled arm to the patient interface module, particular in the wavelength regions surrounding 1450 and 1950 nm. Given the minimum light specifications of the device, a maximum intensity level at particular wavelengths is specified. In addition, a minimum intensity level is supplied in the event that the arm is not near the probe.

For example, given that $I_{1450}$ is the measured intensity of a tissue sample at or near 1450 nm, the following tests are performed: if $I_{1450}>\frac{1}{10}$ of the dynamic range then $f_6=1$. Otherwise $f_6=0$. If $I_{1450}<\frac{1}{1000}$ of the dynamic range then $f_7=1$. Otherwise $f_7=0$. If either $f_6$ or $f_7$ are non-zero, an error is generated. Further, both $f_6$ and $f_7$ are provided to the pattern classification and decision system for diagnosis of the most likely source of error.

Mid-level System

The mid-level 602 system may be divided into sub-levels corresponding to the type of information necessary for analysis. Short-term information includes only the tissue template set. A succeeding sub-level may use patient history associated with the current day and a long-term layer may use the full patient database. A key element of the mid-level system is the usage of the tissue template set to determine if the performance of the instrument and the sampled tissue volume have changed relative to an earlier point in time.

Therefore, detection of errors by the mid-level system can lead to the errors of the low-level system as well as the recollection of the tissue template set.

Spectral Anomalies

Spectral anomalies 609 are caused by perspiration, excessive pressure, poor patient-instrument coupling, application of a skin products, and movement while scanning, and other factors that lead to a mechanical change in the tissue sample. The effects are manifested spectrally through a change in the relative absorbance of various constituents corresponding to a modification of the sampled tissue volume. In particular, the relative absorbance due to constituents at various depths changes as a result of spectral anomalies that result from a change in the optically sampled tissue volume.

Therefore, detection of spectral anomalies is performed on the basis of features from the tissue absorbance spectrum that are extracted, processed and compared to the tissue template and other previously established standards. Features include absolute, first derivative and second derivative magnitude of water, fat, and proteins bands as previously described herein. Processing includes the differences, sums, transformations and ratios of the features.

Figure 16:
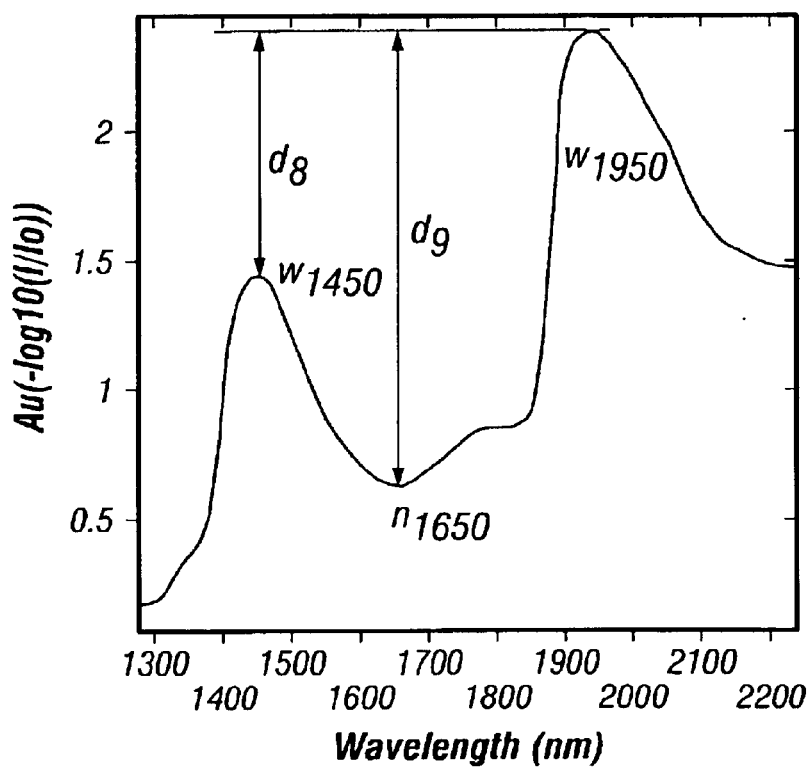
FIG. 16 shows a graph of the absorbance spectrum of FIG. 9 with derived features from water bands at 1450 and 1950 nm identified according to the invention.

In the preferred embodiment of the invention, the acceptability measure used to detect spectral anomalies is determined according to $$f_{m,1}=|(w_{1950}-w_{1450})-(w'_{1950}-w'_{1450})| \tag{10}$$

where $w_{1450}$ is the peak absorbance near 1450 nm and $w_{1950}$ is the peak absorbance near 1950 as specified in FIG. 16 and $w_\lambda'$ refers to the peak absorbance features of the tissue templates absorbance spectrum at wavelength $\lambda$. When a preset limit is exceeded, the sample is rejected.

Surface Contact

Poor surface contact leads to an increase in the surface reflectance and a decrease in the measured absorbance, especially at the water bands. Features associated with this phenomenon are extracted by this module 710 and compared to the related features from the tissue template absorbance spectrum. When the surface contact features deviate significantly from the tissue template or from an a priori level, an error condition results.

The main features include the water bands and their derivatives in the 1100–2450 nm range. When poor contact is made the absorbance of the bands is reduced leading to a reduction in the net analyte signal. If the measured absorbance is significantly lower than the tissue template or exceeds a preset limit an error occurs.

In the preferred embodiment, if the peak absorbance near 1950 nm, $w_{1950}$, (see in FIG. 16) is less than 2.0 Au (absorbance units) then a surface contact error is generated. Second, $w_{1950}$ is compared to the peak absorbance near 1950 nm of the tissue template set absorbance spectrum, $w'_{1950}$ through $$f_{m,2} = \frac{(w'_{1950} - w_{1950})}{w'_{1950}} \quad (11)$$

If $f_{m,2} > 0.1$ a surface contact error is generated. Alternately the water bands near 1150, 1450, or 1820 nm can be used directly or after preprocessing through the first or second derivative to assess surface contact through a comparison with an overall limit and a limit set by the tissue template absorbance spectrum. One skilled in art will appreciate that other limits are set for other wavelengths.

In an alternate embodiment the voltage of the intensity spectrum, I, near the 1450 nm and/or 1950 water bands is compared to a preset maximum level and the level of the tissue template tissue intensity spectrum. If the intensity is significantly higher than either limit a surface contact error is generated. Finally, when a surface contact error is detected the sample is rejected.

Hydration

As discussed previously, changes in the distribution of water in the various compartments lead to changes in the optical properties that are reflected by changes in the spectral features. Therefore, conditions that are detrimental to spectroscopic glucose measurement can be detected by monitoring the selected features and ensuring that their variation over a given measurement period does not exceed that of the calibration set or some other previously established limit.

Hydration 612 is assessed through the relative absorbance of the patient's water bands. Features related to the magnitude of this absorbance are extracted and compared to the tissue template and previously calculated features (over the current day). An error occurs if the patient's hydration has changed substantially from the tissue template.

Figure 11:
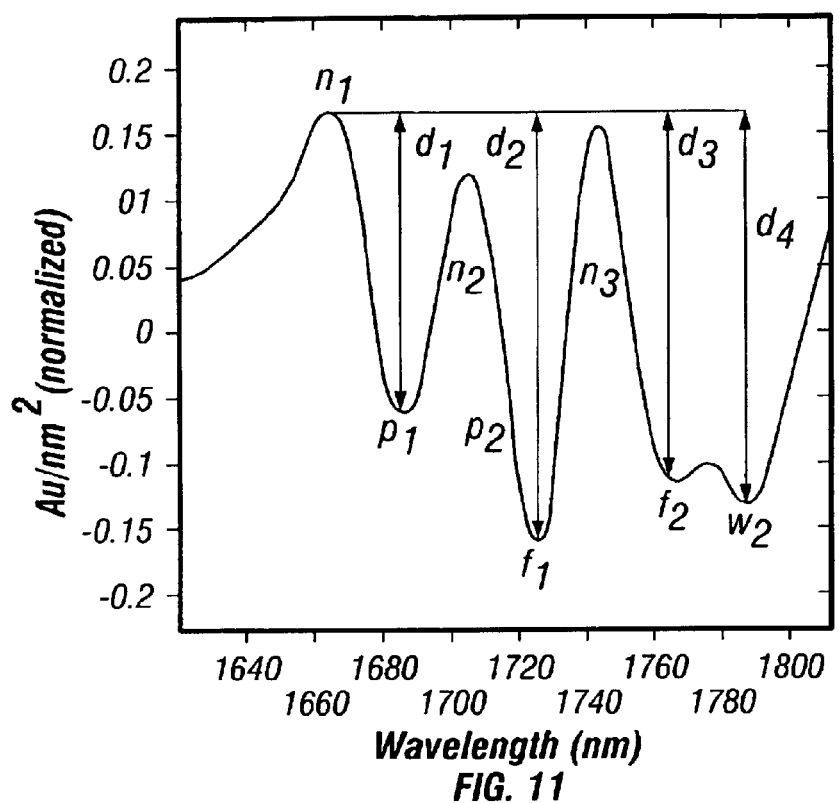
FIG. 11 shows a plot of the second derivative of an absorbance spectrum in the first overtone region with features identified according to the invention.
Figure 12:
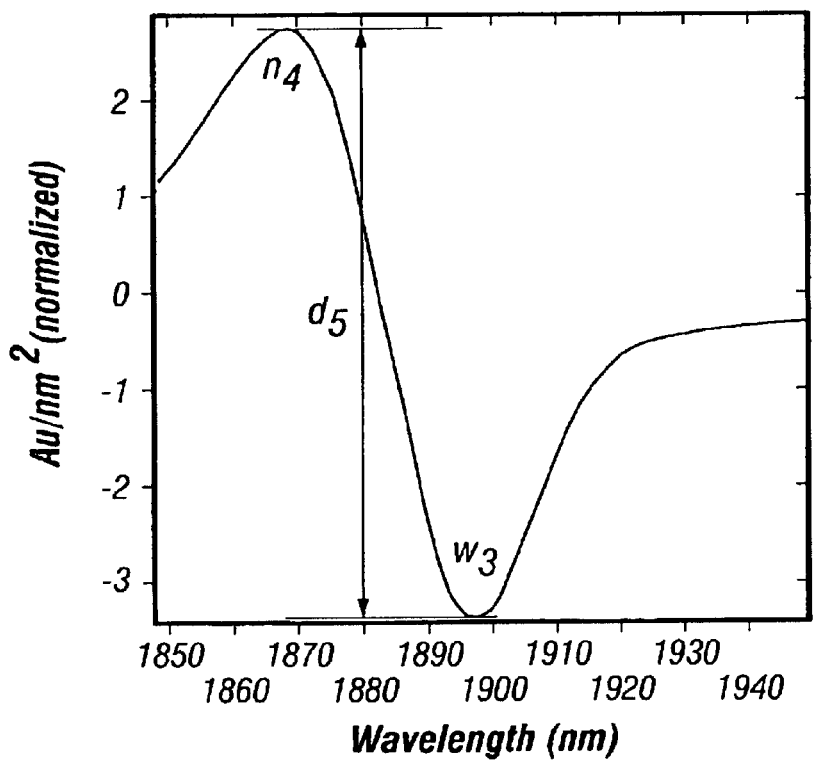
FIG. 12 shows a plot of the second derivative of an absorbance spectrum in vicinity of a water band at 1910 nm with features identified according to the invention.
Figure 13:
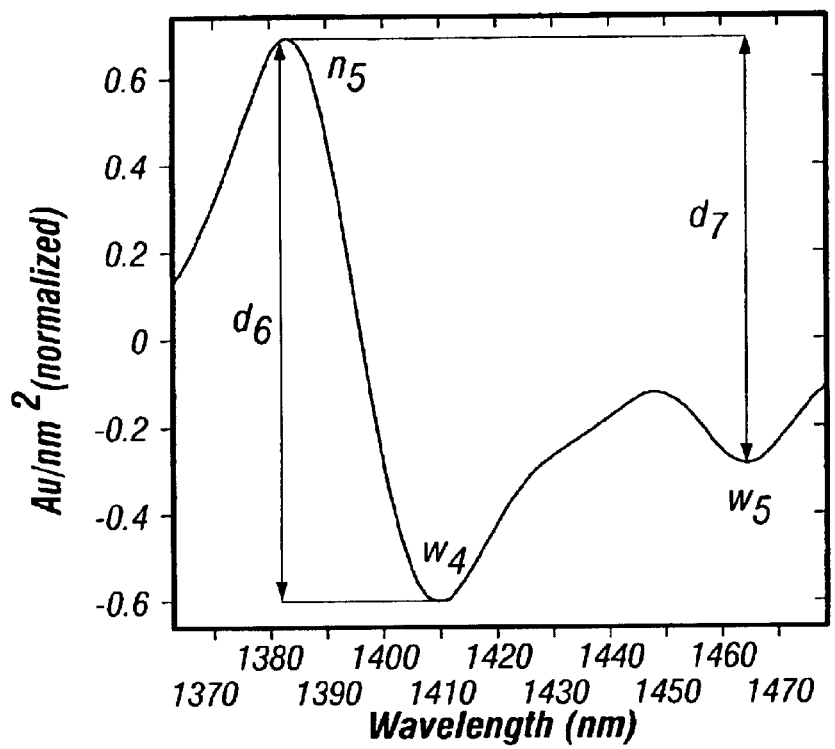
FIG. 13 shows a plot of the second derivative of an absorbance spectrum in vicinity of a water band at 1450 nm with features identified according to the invention.
Figure 14:
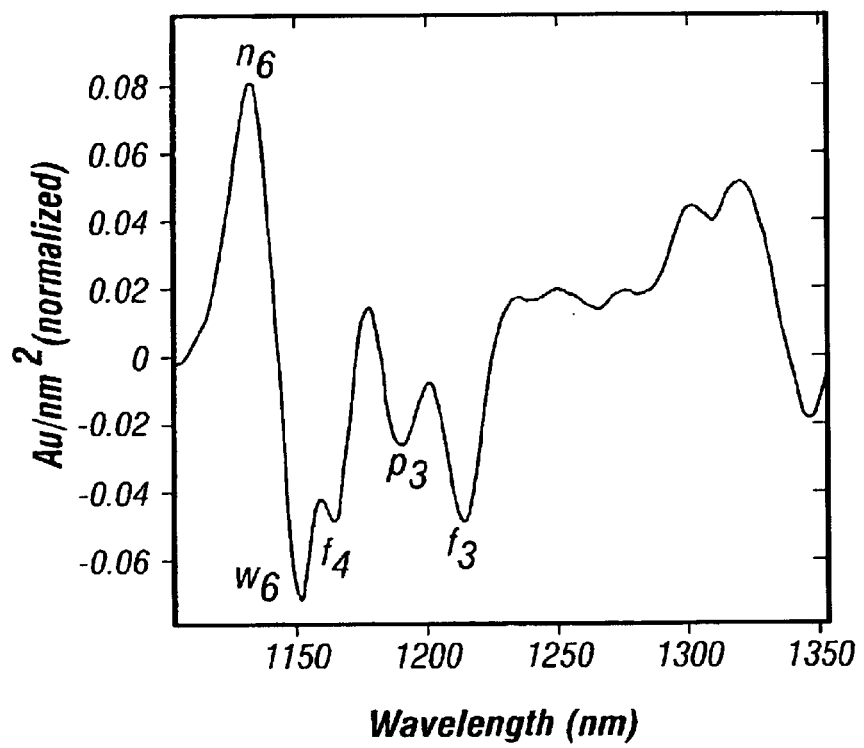
FIG. 14 shows a plot of the second derivative of an absorbance spectrum in the second overtone region with exemplar features identified according to the invention.
Figure 15:
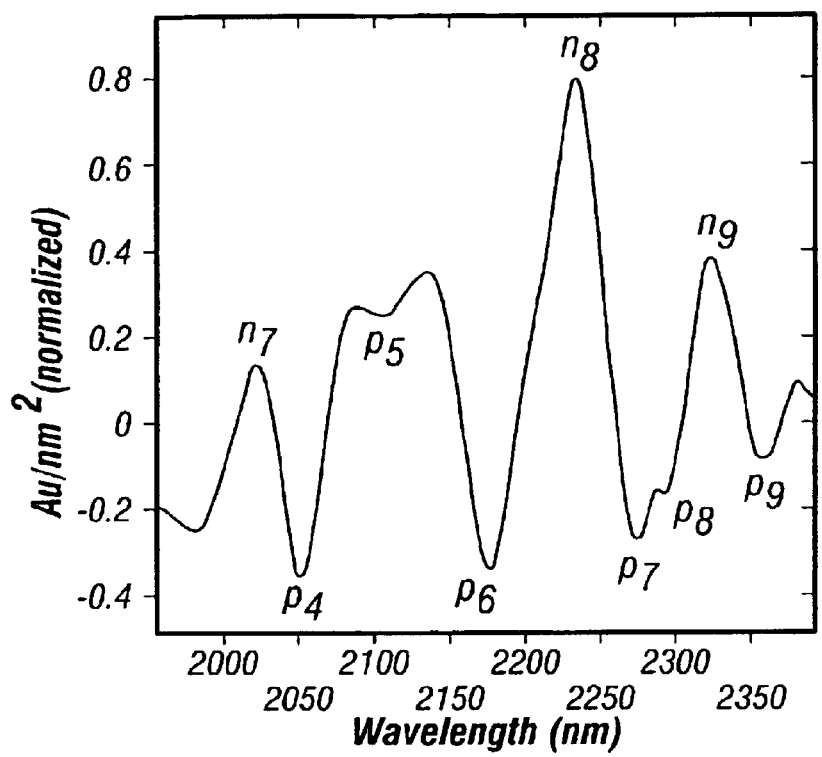
FIG. 15 shows a plot of the second derivative of an absorbance spectrum in the second overtone region with key features identified according to the invention.

In the preferred embodiment, the feature $d_5$ of FIG. 12 is used to represent the hydration state of the tissue sample. A significant absolute deviation from $d_5'$ of the tissue absorbance template is used to indicate a change in hydration. This is detected through the acceptability measure $$f_{m,3} = d_5 - d'_5 \quad (12)$$

and results in an error if the absolute value of $f_{m,3}$ is greater than a preset limit. Alternately, other water bands in the spectrum can be examined for detection of a change in the hydration state of the tissue sample depending upon the targeted depth of penetration. For an averaged estimate of the hydration in a relatively large tissue volume the feature $w_6 - n_6$ shown in FIG. 14 is employed. To detect a change in the surface hydration of the tissue, $d_4$ of FIG. 11 is applied.

In addition, other methods for representing the magnitude of water absorbance can be employed through preprocessing alterations and methods of feature extraction. In an alternate embodiment, the magnitude of the normalized fat band, $d_2(n_{1665} - f_{1727})$, is used to determine hydration state of the dermis. If the magnitude of $d_2$, compared to the tissue template exceeds the total variation or the range established by samples selected to calculate the calibration model, an error is indicated.

If the hydration of the patient has changed, the sample is rejected and the user is prompted for the collection of a new tissue template set.

Sample Variation

Sample variation 613 occurs due to significant mechanical distortion of the optically sampled tissue volume. Given the layered nature of the tissue, such distortion leads to a variation in the relative measured absorbance of key constituents, such as water, fat and protein. Therefore, the method for detecting sample variation is to examine the relative magnitude of features related to the key constituents that are unique to particular layers. In general, the patient absorbance spectrum is preprocessed according to an established method and compared through a distance measure (Euclidean or Mahalanobis) to the preprocessed tissue template. On the basis of the distance, a spectral consistency feature is calculated for evaluation. Spectra exceeding a preset limit are rejected as having excessive sample variation.

In the preferred embodiment of the invention, the spectral consistency is represented by the feature $$f_{m,4} = \frac{d_2}{d_1} - \frac{d'_2}{d'_1} \quad (13)$$

where and $d_1$ and $d_2$ represent the second derivate absorbance of fat and protein respectively shown in FIG. 11 and $d'_1$ and $d'_2$ represent the related tissue template features. An error is generated when the absolute deviation of $f_{m,4}$ exceeds a preset threshold.

Figure 17A:
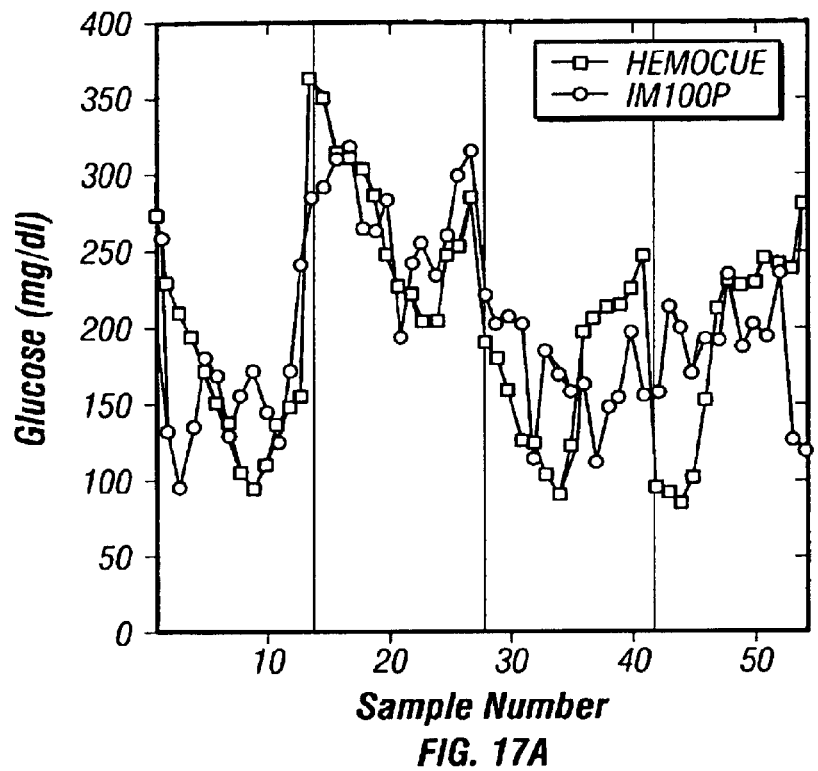
FIG. 17 illustrates an example of error detection through extraction of a tissue consistency feature according to the invention.
Figure 17B:
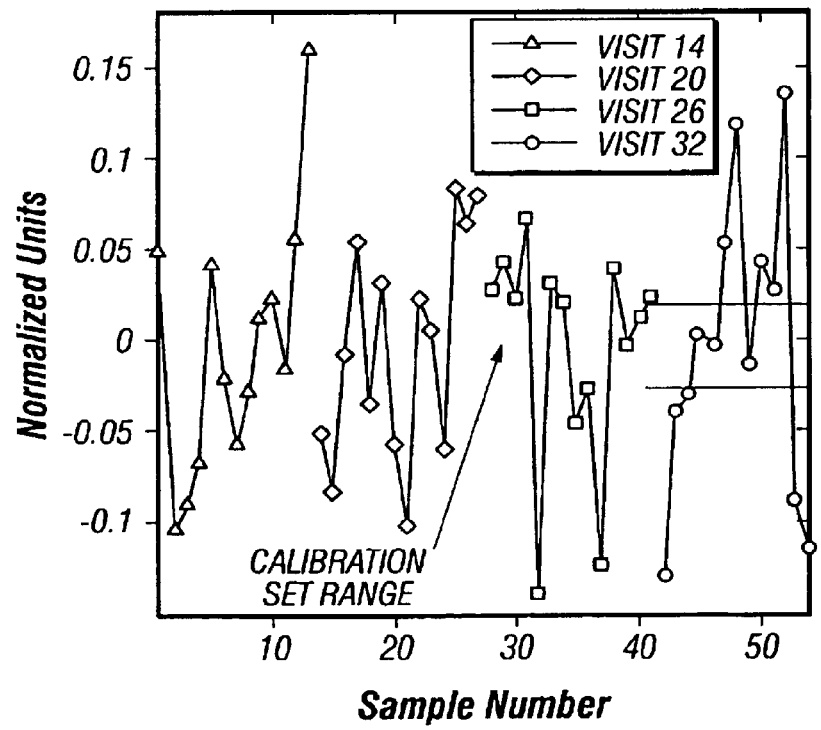

FIG. 17 shows an example of the spectral consistency feature of a patient with poor sampling as compared to a limit established from the calibration set. The poor accuracy of the noninvasive glucose measurements (IM100p) reflects the excessive sample variation.

Sample Transient

A sample transient 614 is a rapid change in either the coupling between the tissue sample site and the patient interface module or a rapid change in the tissue sample. The change causes a profound variation in the M spectra that are collected and a reduction in the net analyte signal related to glucose. Detection of sample transients, therefore, is performed through an examination of the spectra-to-spectra variation in either intensity or absorbance units.

Figure 18A:
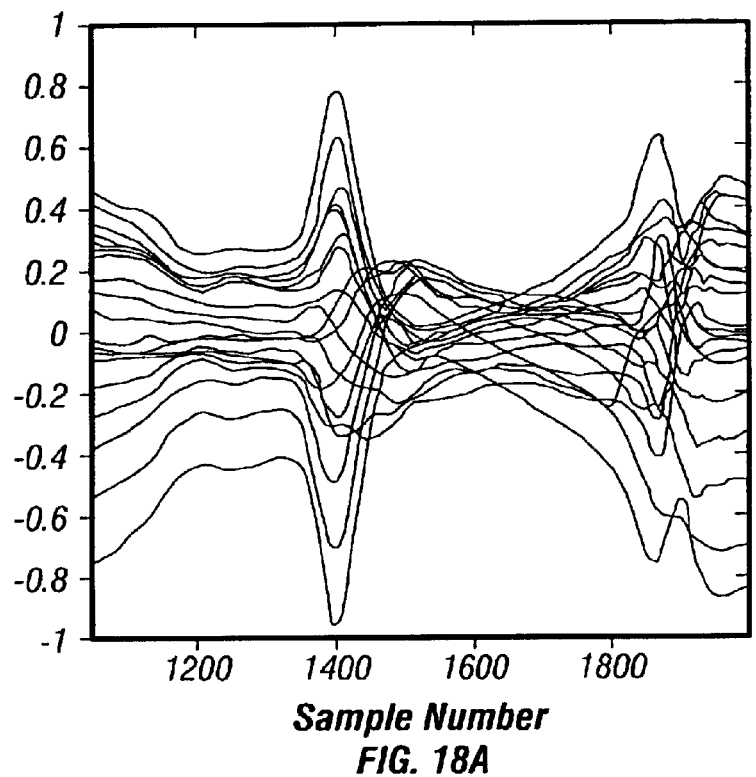
FIG. 18 illustrates detection of sample transients based on comparison of their transients at a particular wavelength according to the invention.

In general, the patient scans are processed and mean-centered to examine their transient behavior. The range and standard deviation at each wavelength is calculated and features are extracted for comparison with a previously established library representing a diversity of error conditions. The error conditions include: arm movement while scanning, perspiration, excessive pressure, poor patient-instrument coupling, tissue distortion, tissue heating, rapid changes in patient physiology, fluid displacement in the tissue and poor sampling conditions. Features exceeding preset limits in each category produce a sample transient error and diagnostic tests are performed to specify the most likely cause of the error. As an example, FIG. 18 shows plots of mean-centered scans associated with one patient sample and the range of the mean-centered scans at one wavelength over a day. The majority of samples produces an error as a result of poor patient-instrument coupling. The acceptability in this case, $f_{m,5}$, is the range of the mean-centered spectra at a particular wavelength. Alternately, the root-mean square variation of mean-centered spectra could be used or other measures that capture the extent of sample variation over a short period of time from a multiplicity of replicate spectra.

Skin Temperature Range (615)

Variations in temperature produce a significant source of spectral interference due to the resulting physiological and chemical variation. Therefore, a change in the temperature of the tissue sample by more than a preset temperature is used to reject a sample.

Figure 19:
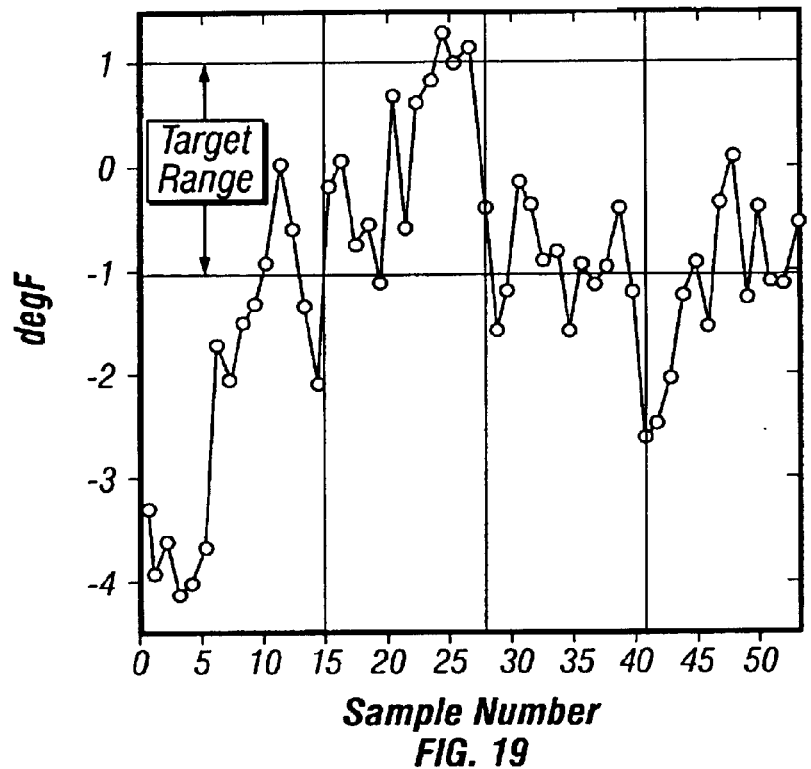
FIG. 19 shows a graph of skin temperature over time with a target range identified according to the invention.

The patient skin temperature is detected either through a direct measurement with a temperature probe or a spectroscopic measurement based on a predetermined skin temperature calibration model. The measured or estimated skin temperature is compared to the skin temperature associated with the tissue template. In the preferred embodiment, skin temperatures falling outside of an allotted range of ±1° F., or that vary significantly from a target range of 86–94° F. produce an error. As an example, FIG. 19 shows a plot of patient skin temperature versus sample number. Samples associated with temperatures outside the target range produce poor noninvasive blood glucose measurements compared to the actual blood glucose concentrations and are therefore detected as outliers.

Sample Consistency and Sample Stability

Sample consistency 616 is ascertained through a comparison of the processed tissue absorbance spectrum with the prior patient scans collected during the day. Sample stability 617 is determined by comparing the level of analyte marker bands to preset limits. Variation that exceeds preset limits produces an error condition. For example, given a tissue spectrum processed through a second derivative, an acceptability measure of performance related to sample consistency and stability is the Euclidean distance from the tissue template.

The essential elements of this procedure are the following:

Given a tissue template in the form of a tissue absorbance spectrum collected at some point prior in time and given a new tissue absorbance spectrum;

Process both spectra in the same manner to reduce unwanted variation;

Select a wavelength range (e.g., 1250–1900 nm);

Calculate a mathematical measure of the similarity or dissimilarity between the two denoted $f_{m,6}$. Examples of the possible measures include the correlation coefficient, Euclidean distance, Mahalanobis distance and pattern matching algorithms; and If the newly collected sample differs substantially from the tissue template an error condition results.

Tissue Transients

Tissue transients 618 are detected by examining the time-history of features that are sensitive to changes in the physiological state of the patient, systematic changes in the local tissue morphology (e.g., fluid shifts) and systematic patient-instrument coupling errors. Features related to known fat, protein, and water bands are extracted from the absorbance spectrum and processed. When the range and time related correlation of a feature exceeds a predetermined limit an error condition occurs.

In the preferred embodiment of the invention, a tissue transient is detected on the basis of the fat band, $d_2$, shown in FIG. 11. The tissue transient feature is determined through $$f_{m,7}=d_2-d'_2 \quad (14)$$

where $d_2$ is the second derivate absorbance of fat and $d'_2$ represents the related tissue template features. An error is generated when the absolute deviation of $f_{m,7}$ exceeds a preset threshold.

Figure 20A:
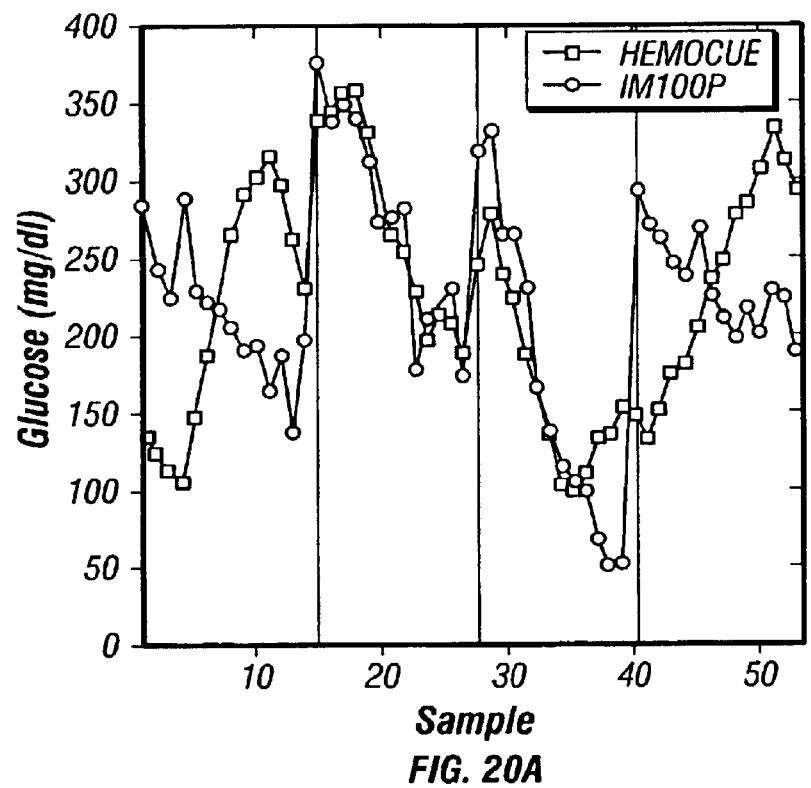
FIG. 20 illustrates detrimental effect of tissue transients on noninvasive glucose measurement according to the invention.
Figure 20B:
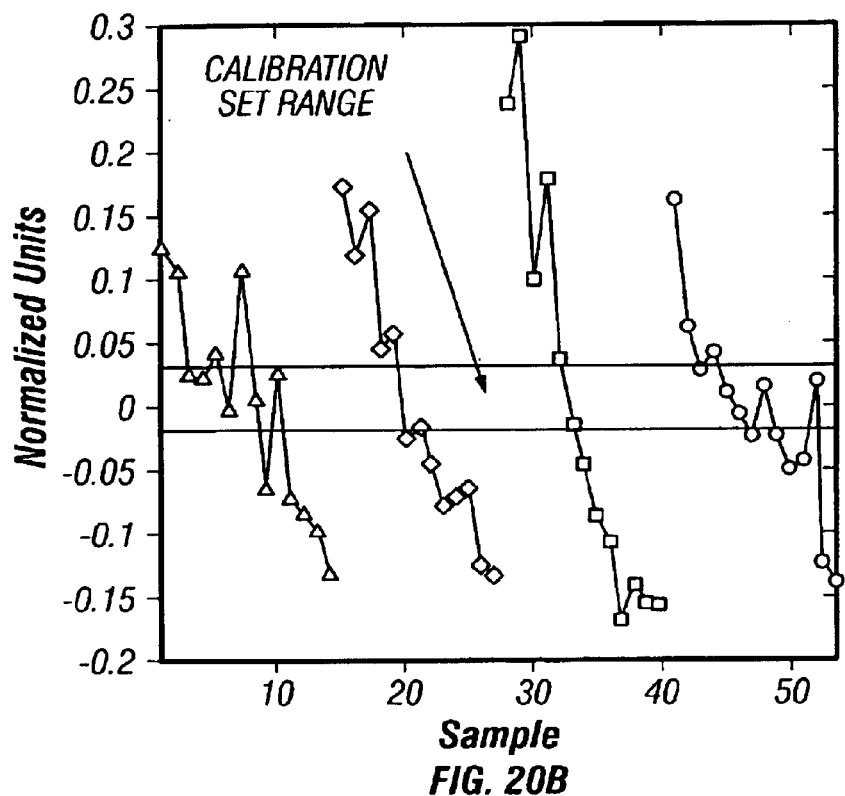

For example, FIG. 20 shows a plot of a tissue transient feature over several days from one patient. The variation of the feature exceeds the limits established by the calibration set and significantly degrades the noninvasive glucose measurement performance of the instrument.

Skin Temperature Transients (619)

Excessive variation in skin temperature reduces the accessibility of the net analyte signal related to glucose. The error detection system includes a skin temperature calibration capable of detecting the patient's skin temperature spectroscopically.

Figure 21A:
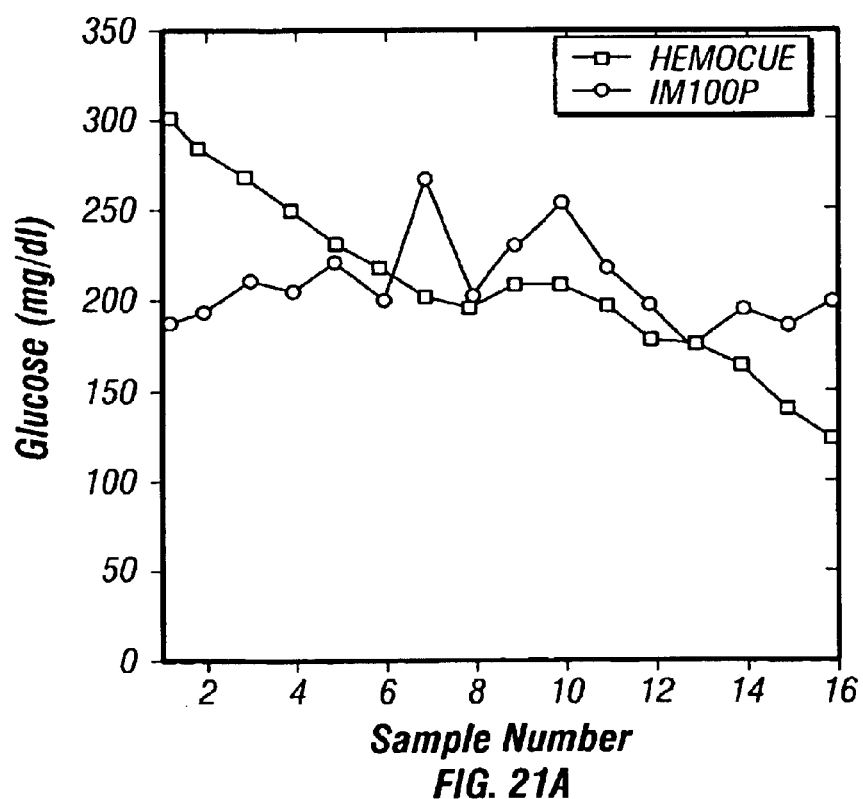
FIG. 21 illustrates detrimental effect temperature transients on noninvasive glucose measurement according to the invention.
Figure 21B:
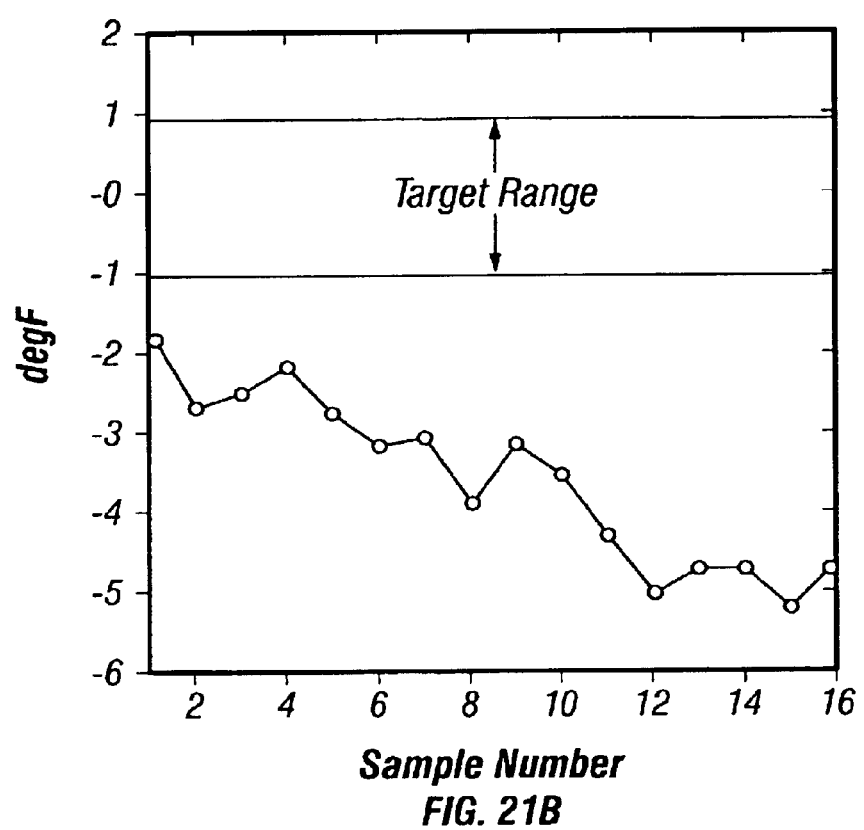

Detection of skin temperature transients is performed by comparing the range and time correlation of the measured skin temperature over the samples collected subsequent to the tissue transient. FIG. 21 shows the detrimental effect of a skin temperature transient that was detected as both out of range and highly correlated with time. The plotted noninvasive measurement (IM100 p) and reference glucose measurements (Hemocue) show the skin temperature transient has led to an attenuation of the signal attributable to glucose. If the range exceeds a pre-set boundary by ±1 degree, or if the temperature exhibits a unidirectional change, an error condition results.

Data Consistency (621)

A comparison between the patient database and the spectral samples is performed by the Data Consistency module. If the spectral variation is inconsistent with historical data an error condition is generated.

Sample Structure (622)

The sample structure refers to the varying characteristics of the tissue sample that are spectrally manifested through distinct analyte absorption features. Aging, environmental exposure and health and lifestyle changes can lead to marked differences in the scattering properties of the tissue due to the redistribution fluids, degradation of proteins and increase or decrease in trigylceride concentration in adipose tissue. Large deviations in the tissue sample site may also lead to an apparent change in the Sample Structure due to the heterogeneity and diverse spatial morphology of tissue. Finally, the detection of large variation in the Sample Structure Module may indicate that someone other than the target patient is using the device.

Changes in the sample structure are detected through the comparison of a set of distinct features, called the "tissue fingerprint", with those in the patient database. Excessive differences in new data lead to an error condition.

In the preferred embodiment, the first generated tissue template absorbance spectrum associated with a particular patient is stored by the software system in a database. On subsequent visits, a set of derived features from the tissue template and each newly generated tissue template are compared by means of the pattern matching system. The process is implemented as follows:

Given the original tissue template in the form of a tissue absorbance spectrum and a new tissue absorbance spectrum or a new tissue template absorbance spectrum;

Process both spectra in the same manner to reduce unwanted variation. In the preferred embodiment this is performed through the second derivative;

Select a wavelength range (e.g., 1150:1350 or 1650–1850 nm);

Calculate a mathematical measure of the similarity or dissimilarity between the two, denoted $f_{m,7}$. Examples of the possible measures include the correlation coefficient, Euclidean distance, Mahalanobis distance and pattern matching algorithms;

If the newly collected sample differs substantially from the original tissue template an error condition results;

An error generated by this sub-module indicates a gross change in the sampled tissue volume.

Instrument Drift (611)

Instrument drift is monitored by comparing performance parameters (for example, light intensity of the reference spectrum) to data collected with the tissue template. Excessive drift is detrimental to the noninvasive glucose measurement due to the distortion of the measured spectrum. An error condition is generated if the instrument is outside preset operating parameters. For example, the peak intensity of the reference scan is monitored throughout the course of a measurement period. If the intensity varies by more than 0.1% of the reference spectrum associated with the tissue template an error is generated.

Instrument Stability (620)

Instrument Stability is evaluated by comparing the measured spectra with data from a history file containing instrumental parameters including RMS noise, wavelength shift and signal intensity. This history file is used to determine if the instrument performance has changed over a short time frame (one-day).

Instrument Performance (623)

Long-Term Instrument Performance is evaluated through determination and monitoring of instrument noise, temperatures, wavelength stability, and signal intensity over the life of the instrument. This is used to monitor subtle changes in an instrument and the impact that it has on the measurement and predict potential instrument related failures.

High-level Errors

High-level 603 error testing consists of the most sophisticated tests and relies on the data used in the low-level and mid-level systems as well as the calibration model and parameters related to the calibration model.

Classification (624)

Previously we described a method and apparatus for determining a suitable patient class for calibration on the basis of a calibration database. Patient data falling outside the classified set are termed outliers. This is described in detail in Malin, et al., supra and S. Monfre, T. Blank, T. Ruchti, S. Thennadil, *A multi-tier method of classifying sample spectra for non-invasive blood analyte prediction*, U.S. patent application Ser. No. 09/665,201, filed on Sep. 18, 2000.

Calibration Set Comparison (625)

Noninvasive glucose measurements determined from spectra that are inconsistent with the structure and variance of the calibration set have a higher probability of being inaccurate. Therefore, a comparison between the patient data collected and the calibration set is performed through feature extraction (e.g., principal components analysis) and/or cluster analysis to determine the consistency of the spectral measurement with data used to generate the calibration model. Patient data falling outside the range of calibration induce an error condition.

In the preferred embodiment, the detection of spectral outliers is performed through a principal components analysis and an analysis of the residuals. First, a newly acquired spectrum, a, is processed and then projected onto a set of eigenvectors, contained in the matrix O, that were developed through a principal components analysis on the calibration set. The processing of the data is performed through the following steps: processing through a first derivative FIR filter, multiplicative scatter correction, wavelength selection, and offset adjustment via the processed tissue template absorbance spectrum. The number of eigenvectors varies from 2–15 and is dependent on the specific calibration set. The projection of the processed spectrum, x, onto the eigenvectors proceeds according to $$xpc^o = xO \quad (15)$$

and produces the 1 by P vector of scores, $xpc_o$. The residual, $f_{h,1}$, is determined according to $$f_{h,1} = \|x - xpc_o O^T\| \quad (16)$$

An error condition occurs if the result is greater than three times the standard deviation of the expected residual (of the calibration set).

Instrument Operation (629)

The operational state of the instrument is compared to similar instruments including the instrument used to collect the calibration data. A large database containing history information from similar instruments is pooled to compare the characteristics of the current instrument to those of past instruments.

Measurement Precision (626)

Figure 18B:
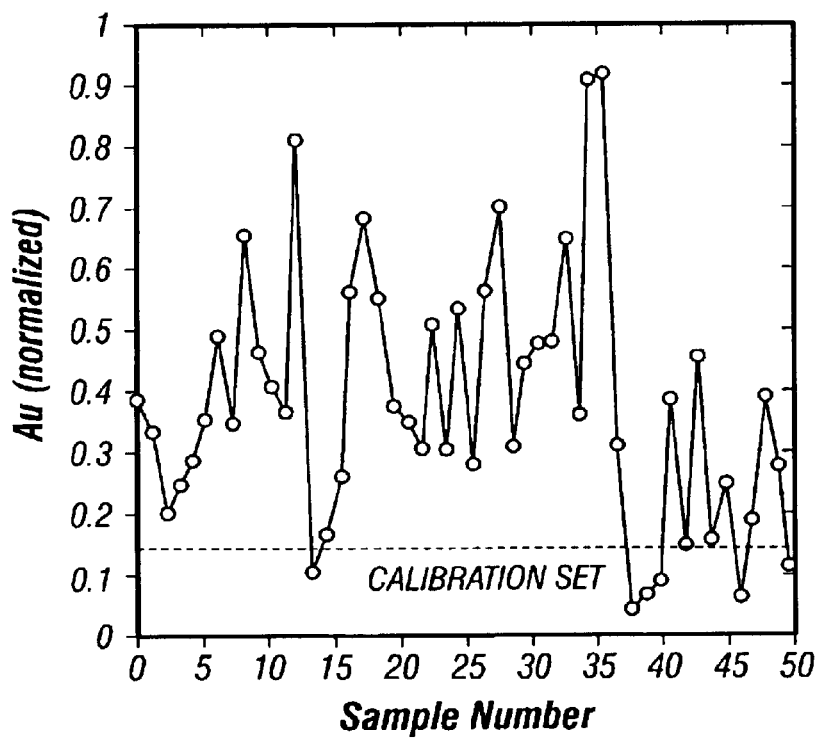

Application of the calibration model to each of the M tissue near-infrared mesurement replicates enables an estimate of the measurement precision. Widely varying samples, such as those shown in FIG. 18A, lead to excessive variation in the associated glucose measurement (FIG. 18B). The range, trend and standard deviation of the glucose measurements associated with a set of replicates are compared with a maximum acceptable value and the sample is rejected accordingly. In particular, this method provides an estimate of the confidence (precision) of the final averaged glucose measurement.

In the preferred embodiment, a set of replicate glucose estimates is obtained through $$\hat{y}_k = x_k G + b \quad (17)$$

where $\hat{y}_k$ is the noninvasive glucose estimate associated with the kth replicate absorbance spectrum, $x_k$ is the preprocessed absorbance spectrum associated with the kth replicate and G and b are parameters of the calibration model. A series of three tests are implemented according to the following figures of merit $$f_{h,2} = \max(\hat{y}) - \min(\hat{y})$$
$$f_{h,3} = std(\hat{y}) \quad (18)$$
$$f_{h,4} = |slope(\hat{y})|$$

where slope refers to an estimate of the slope of the N elements of $\hat{y}$ versus replicate number. Error detection occurs by comparing each of the acceptability measures in equation 17, above, to a maximum value.

Measurement Range (627)

The measurements associated with the replicate spectra scans are averaged to yield a final glucose measurement. If the measurement is outside a preset range (e.g. 50–400 mg/dL) an error results.

Expected Value (628)

The expected value sub-module uses prior glucose measurements to detect potentially erroneous non-invasive glucose measurements through prediction models. The models utilize the time series of past glucose measurements to extrapolate a future prediction. This prediction is compared with the measurement obtained from a newly acquired spectral measurement. When the result of the comparison is a large discrepancy and the prediction has a high degree of certainty an error is generated. For example, when a series of non-invasive glucose measurements over a period of time systematically decrease in one direction toward 100 mg/dL and within a short period of time a non-invasive glucose measurement of 350 mg/dL is obtained, the suspicious value is flagged as potentially erroneous.

The certainty of the prediction depends on the quality of the model, the times series data and whether or not other perturbing variables are observable. For example, if the patient has not collected glucose measurements at regular intervals leading up to a new measurement, the prediction by a model will be uncertain. If the error detection system is given knowledge of insulin usage, the patient's history and carbohydrate consumption a more accurate model can be developed.

In the preferred embodiment, the time series of glucose measurements is modeled as an autoregressive integrated moving average (ARIMA) process that provides both a prediction and a confidence interval (see G.E.P. Box, G. M. Jenkins and G. Reinsel, *Time Series Analysis,* Third Edition, Englewood Cliffs, N.J.: Prentice Hall, 1994, p. 112). Alternately, a simple linear interpolation is performed on the basis of the closes 2–5 measurements. In addition, a Kalman filter (see Goodwin, G. C. and K. S. Sin, *Adaptive Filtering and Control,* Englewood Cliffs, N.J.: Prentice-Hall, Inc., 1984) with a forgetting factor is used to model the noninvasive glucose measurements on the basis of past measurements. Finally, when carbohydrate consumption and insulin dosages are available, pharmacokinetic models are employed to obtain glucose predictions.

The prediction model is used to obtain a prediction, $\hat{y}_p \pm C$. If a new glucose measurement is beyond the confidence interval, C, of $\hat{y}_p$, the measurement is considered uncertain.

State Classification and Rule-based Decision System

Figure 3:
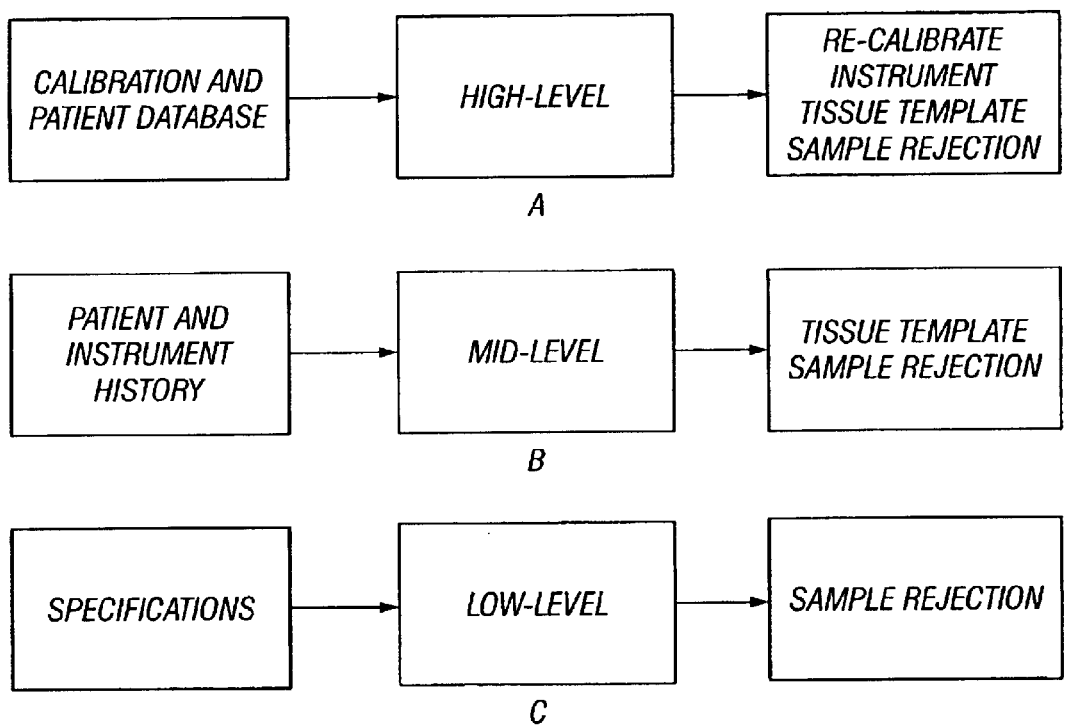
FIG. 3 provides a block diagram of an alternate embodiment of the system of FIG. 2, wherein levels are applied individually, or in any combination according to the invention.

A state-classification and rule-based decision system 800, shown in FIG. 8, collects the acceptability measures 801 of the sub-modules, (optionally) normalizes them 802, reduces each level of error to a set of key states 804 and then provides the states to a rule-based engine 805 for mapping to a decision 806. The system is split into three levels corresponding to those of FIG. 2 and FIG. 3, according to the nature of the data and level of sophistication of each level.

The function of the system is to detect erroneous measurements from a systems level that would not be normally detected and to diagnose the potential source of the error based on a multiplicity of performance measures. To avoid false positives, each individual sub-component that performs error detection is configured and parameterized such that an erroneous measurement is detected when an extreme or "outlier" condition occurs. Even the sophisticated processes implemented in the high-level portion of FIG. 3 will miss errors that result from a more subtle or systematic failure mode. The system exploits the redundancy of information across the measures of acceptability and the benefit of pattern recognition to detect modes of failure that are not obvious to any single sub-component of the system.

In essence, the system uses pattern recognition to detect conditions that are not conducive to noninvasive measurement of glucose. The system exploits a multiplicity of sub-systems or "sensors", each of which provide a measure of acceptability according to a specific test. The acceptability measures 801, denoted previously by $f_{level, component}$, are the inputs to the system 800.

A classifier 803 determines one or more operating states for each "Level," as defined previously. Finally, the operating states are used in conjunction with a rule-based system to provide a decision 806 regarding the potential acceptability of the glucose measurement.

The goal of the classification step is to determine the operating state that reflects the status of the noninvasive tissue measurement. In this step the sample is assigned to one or more of many predefined classes for which a state has been predefined.

The development of the classification system requires a data set of exemplar spectral measurements 807 from a representative sampling of the population. Class definition is the assignment of the measurements in the exploratory data set to classes. After class definition, the measurements and class assignments are used to determine the mapping from the features to class assignments.

Class definition may be performed through either a supervised or an unsupervised approach [Schurmann, J. Pattern Classification. *A Unified View of Statistical and Neural Approaches.* John Wiley & Sons, Inc., New York, 1996.]. In the supervised case, classes are defined through known differences in the data. The use of a priori information in this manner is the first step in supervised pattern recognition that develops classification models when the class assignment is known.

Unsupervised methods rely solely on the acceptability measures to explore and develop clusters or natural groupings of the data in feature space. Such an analysis optimizes the within cluster homogeneity and the between cluster separation. Clusters formed from features with physical meaning can be interpreted based on the known underlying phenomenon that is causing variation in the feature space. However, cluster analysis does not utilize a priori information and can yield inconsistent results.

In either approach, the method of optimization is associated with the quality of the noninvasive glucose measurement compared to a known reference measurement (e.g., an electrochemical analysis of a capillary blood draw).

For example, a large set of samples (spectral data) from a multiplicity of subjects is used to create a database containing acceptability measures, noninvasive glucose measurements and reference glucose measurements. The acceptability measures are sorted according to the level of sophistication as discussed previously. Within each level of sophistication an abstract factor analysis is performed to account for the redundancy of information represented by the acceptability measures and a cluster analysis is performed to identify states that are associated with various levels of measurement error. Finally, the states, or various classes are combined and are used to provide an error diagnosis; for example:

Acceptable Measurement;

Instrument Error;

Sample Error;

Temperature Control Problem;

Instrument Malfunction;

Obsolete Tissue Template;

Improper Patient Interface Configuration;

Tissue Change; and

Patient Out of Calibration.

Under each category of problems, sub-categories may be created, for example when dealing with results from a large data set.

While the levels of sophistication have been used within the classification system, this is not ultimately necessary and, given enough exemplary data and a priori knowledge, a single classification system could be employed.

In an alternate method, a smaller data set is created through the introduction of errors associated with the categories defined above and a statistical classified is employed to map the acceptability measures to a final decision. In this embodiment the classifier is designed by determining an optimal mapping or transformation from the feature space to a class estimate that minimizes the number of misclassifications. The form of the mapping varies by method as does the definition of "optimal". Existing methods include linear discriminant analysis [Duda, R. O. and P. E. Hart, *Pattern Classification and Scene Analysis,* John Wiley and Sons, New York, 1973], SIMCA [Wold, S. and M. Sjostrom. "SIMCA: A method for analyzing chemical data in terms of similarity and analogy," *Chemometrics: Theory and Application,* ed. B. R. Kowalski, ACS Symposium Series, 52, 1977.], k nearest-neighbor [Duda, R. O. and P. E. Hart, *Pattern Classification and Scene Analysis,* John Wiley and Sons, New York, 1973] and various forms of artificial neural networks [Haykin, S., *Neural Networks: A Comprehensive Foundation,* Upper Saddle River, N.J.: Prentice-Hall, 1994.].

While statistically based class definitions provide a set of "crisp" class definitions the measurement modes leading to error are manifested by a continuous gradient in the acceptability measures. Therefore, the classes defined previously overlap and distinct class boundaries do not necessarily exist in all cases.

In a third embodiment of the system, class assignment and decisions are based on fuzzy set theory [Chen, C. H., ed., Fuzzy Logic and Neural Network Handbook, Piscataway, N.J.: IEEE Press, 1996],[Pao, Y. H. *Adaptive Pattern Recognition and Neural Networks.* Addison-Wesley Publishing Company, Inc., Reading, Mass., 1989.]. Generally, membership in fuzzy sets is defined by a continuum of grades and a set of membership functions that map the feature space into the interval [0,1] for each class. The assigned membership grade represents the degree of class membership with "1" corresponding to the highest degree. Therefore, a sample can simultaneously be a member of more than one class.

The mapping from feature space to a vector of class memberships is given by $$c_k = g_k(f) \quad (19)$$

where k=1, 2, ... P, $g_k(\cdot)$ is the membership function of the kth class, $c_k \in [0,1]$ for all k and the vector $c \in \Re^P$ is the set of class memberships. The membership vector provides the degree of membership in each of the predefined classes.

The design of membership functions utilizes fuzzy class definitions similar to the methods previously described. Fuzzy cluster analysis can be applied and several methods, differing according to structure and optimization approach can be used to develop the fuzzy classifier. All methods attempt to minimize the estimation error of the class membership over a population of samples.

Conclusion

An Intelligent System for Detecting Errors and Determining Failure Modes for Noninvasive Measurement of Blood Glucose has been developed and reported. Application of the system in the noninvasive glucose sensor produces superior results through the identification of faulty samples and the diagnosis of the problem source.

Although the invention has been described herein with reference to certain preferred embodiments, one skilled in the art will readily appreciate that other applications may be substituted for those set forth herein without departing from the spirit and scope of the present invention. Accordingly, the invention should only be limited by the claims included below.

What is claimed is:

1. An intelligent system for detecting errors in spectroscopic determination of blood and/or tissue analytes comprising:

an apparatus for measuring a spectrum at a selected tissue site on a subject; and an error detection system (EDS), said EDS comprising any of:

one or more individual modules, a module embodying at least one of a plurality of methods for detecting errors in spectral measurements; and one or more subsystems, a subsystem comprising a plurality of said individual modules having a commonality; wherein said one or more modules and said one or more subsystems are combined to form:

a hierarchic system comprising at least one level, a level comprising one of: at least one subsystem, at least one module, and a combination of at least one subsystem and at least one module;

said EDS further comprising an error manager;

wherein said intelligent system detects conditions unsuitable for analyte determination.

2. The system of claim 1, wherein said modules output an acceptability measure, each module having a range of acceptability specified for its associated acceptability measure, wherein said ranges of acceptability are based on a set of exemplary samples, the set containing both erroneous measurements of known origin and valid measurements; and wherein an acceptability measure outside of its associated range of acceptability constitutes an error.

3. The system of claim 1, wherein said apparatus for measuring a spectrum comprises a spectrometer instrument.

4. The system of claim 1, wherein said analyte comprises glucose.

5. The system of claim 1, wherein measurement is any of noninvasive and in vivo.

6. The system of claim 1, further comprising a preprocessing and feature extraction system.

7. The system of claim 6, wherein said preprocessing and feature extraction system comprises:

means for low-level processing of raw intensity spectra, spectra including sample spectra and reference spectra;

means for averaging processed intensity spectra;

means for calculating an absorbance spectrum from said averaged, processed intensity spectra;

means for preprocessing said absorbance spectrum;

means for extracting features from a preprocessed absorbance spectrum;

a tissue template set, the tissue template comprising a set of measurements taken at onset of a measurement period; and a calibration model, said calibration model applied to any of said preprocessed absorbance spectrum and extracted features to measure said analyte, said calibration model also applied to estimate relative precision of a measurement and/or determine certainty of a measurement in view of past measurements.

8. The system of claim 7, wherein low-level processing includes subtraction of an electrical offset from said raw intensity spectra.

9. The system of claim 7, wherein averaging includes any of:

simple average calculation; and robust estimation of mean intensity at each wavelength.

10. The system of claim 7, wherein said absorbance spectrum comprises a specific set of wavelengths in the near IR region that has been optimized for feature extraction and measurement.

11. The system of claim 7, wherein preprocessing includes any of:

scaling;

normalizing;

smoothing;

derivatizing;

filtering; and transformations that attenuate noise and instrumental variation without unduly affecting signal of interest.

12. The system of claim 7, wherein said features include any of:

simple features, comprising values of a processed spectral measurement at which slope equals zero;

derived features, comprising additional features derived from simple features through mathematical transformation; and abstract features developed through linear and/or nonlinear transformations of said preprocessed spectrum.

13. The system of claim 12, wherein simple features include any of:

critical points;

normalization points;

fat band points;

protein band points; and water band points.

14. The system of claim 13, wherein derived features are mathematically derived from said critical, normalization, fat band, protein band, and water band points.

15. The system of claim 12, wherein abstract features do not have a specific interpretation related to a physical system, abstract features including scores from a principal components analysis.

16. The system of claim 7, wherein said tissue template set includes any of:

intensity spectra for sample and reference;

an absorbance spectrum;

a preprocessed absorbance spectrum;

and a set of extracted features.

17. The system of claim 1, said intelligent system further comprising a state classification and rule-based decision system.

18. The system of claim 17, wherein said state classification and rule-based decision system comprises:

means for collecting acceptability measures from said modules;

means for normalizing said acceptability measures;

a classifier, wherein said classifier determines at least one operating state for each of said levels; and a rule-based decision engine, wherein a decision is made regarding acceptability of an analyte measurement based on said determined operating states.

19. The system of claim 18, wherein said classifier is developed from a data set of exemplary spectral measurements from a representative population sample.

20. The system of claim 19, wherein classes are defined by assigning said measurements from said data set to classes.

21. The system of claim 19, wherein class definition employs a supervised approach, wherein classes are defined through known differences in the data.

22. The system of claim 19, wherein class definition employs an unsupervised approach, wherein said acceptability measures are used to explore and develop clusters of the data in feature space, so that within cluster homogeneity and between cluster separation is optimized.

23. The system of claim 22, wherein a large set of samples from a multiplicity of subjects is used to create a database, the database including acceptability measures, measurements, and reference measurements.

24. The system of claim 23, wherein acceptability measures are sorted according to level of sophistication.

25. The system of claim 24, wherein an abstract factor analysis is performed to account for redundancy of information presented by said acceptability measures; and wherein a cluster analysis is performed to identify classes, said classes constituting states, that are associated with various levels of measurement error.

26. The system of claim 25, wherein states are combined to provide an error diagnosis.

27. The system of claim 22, wherein said data set is created through introduction of errors associated with defined categories, and wherein a statistical classifier is used to map said acceptability measures to a final decision.

28. The system of claim 22, wherein said classifier is designed by determining an optimal mapping from feature space to a class estimate that minimizes misclassifications.

29. The system of claim 22, wherein statistically based class definitions provide crisp class definitions.

30. The system of claim 19, wherein class assignment and decisions are based on fuzzy set theory.

31. The system of claim 30, wherein membership in fuzzy sets is defined by a continuum of grades and a set of membership functions that map feature space into an interval for each class, wherein assigned membership grade represents a degree of class membership, so that a sample can simultaneously be a member of more than one class.

32. The system of claim 1, wherein said modules include any of:

an online error check module;

an instrument error-detection module;

an instrument QC (quality control)-checking module;

a signal-processing module;

a sampling error-detection module;

a spectral anomaly-detection module;

surface contact error-detection module;

a hydration-checking module;

a sample variation-detection module;

a sample transient-detection module;

a patient skin temperature-measuring module;

a sample consistency-assessment module;

a sample stability-assessment module;

a tissue transient-detection module;

a skin temperature transient-detection module;

a data consistency module;

a sample structure variation-detection module;

an instrument drift-monitoring module;

an instrument stability-monitoring module;

an instrument performance-monitoring module;

a classification module;

a calibration set-comparison module;

an instrument operation-comparison module;

a measurement precision-estimation module;

a measurement range-assessment module; and an expected value-prediction module.

33. The system of claim 32, wherein subsystems are defined according to sophistication of included modules, said subsystems including any of:

a low-level subsystem;

a mid-level subsystem; and a high-level subsystem.

34. The system of claim 33, wherein said low-level subsystem includes modules for testing data immediately after collection of reference and sample spectra, said spectra comprising intensity spectra.

35. The system of claim 34, wherein testing is based on acceptability specifications for noninvasive glucose measurement, and wherein an action resulting from deviation from a specified level of acceptability includes any of:
   rejection of a collected spectrum;
   rejection of a tissue sample; and
   generation of an instrument malfunction error.

36. The system of claim 33, wherein said low-level subsystem includes any of:
   the online error check module;
   the instrument error detection module;
   the instrument QC-checking module;
   the signal processing module; and
   the sampling error detection module.

37. The system of claim 33, wherein a system manager inputs instrument performance specifications and target spectra for each type of material to be scanned to said low-level subsystem.

38. The system of claim 37, wherein said specifications include any of:
   noise limits;
   minimum operating temperature limits;
   maximum signal levels;
   wavelength accuracy limits; and
   precision limits.

39. The system of claim 33, wherein said mid-level subsystem comprises a plurality of sublevels, said sublevels corresponding to type of information necessary for analysis.

40. The system of claim 33, wherein said mid-level subsystem uses a tissue template to determine if instrument performance and/or a sampled tissue volume have changed relative to an earlier time.

41. The system of claim 33, wherein said mid-level subsystem includes any of:
   the spectral anomaly-detection module;
   the surface contact error-detection module;
   the hydration-checking module;
   the sample variation-detection module;
   the sample transient-detection module
   the patient skin temperature-measuring module
   the sample consistency-assessment module;
   the sample stability-assessment module
   the tissue transient-detection module;
   the skin temperature transient-detection module;
   the data consistency module;
   the sample structure variation-detection module;
   the instrument drift-monitoring module;
   the instrument stability-monitoring module; and
   the instrument performance-monitoring module.

42. The system of claim 33, wherein actions taken by said mid-level subsystem include any of:
   instrument maintenance;
   recollect tissue template;
   sample rejection; and
   instrument QC check.

43. The system of claim 33, wherein said high-level subsystem relies on:
   a calibration model and parameters relating to the calibration model;
   a patient database;
   patient history;
   a tissue template; and
   measurement specifications common to all instruments and all patients.

44. The system of claim 33, wherein said high-level subsystem includes any of:
   the classification module;
   the calibration set-comparison module;
   the instrument operation-comparison module;
   the measurement precision-estimation module;
   the measurement range-assessment module; and
   the expected value-prediction module.

45. The system of claim 33, wherein actions taken by said high-level subsystem include any of:
   change calibration model;
   recalibrate patient;
   instrument failure;
   invalid glucose measurement;
   instrument maintenance;
   recollect tissue template;
   sample rejection; and
   instrument QC check.

46. The system of claim 33, wherein levels of said hierarchic system receive and inherit information from lower levels.

47. The system of claim 46, wherein errors generated at each level are inherited by succeeding levels for error diagnosis until a critical error is encountered.

48. The system of claim 46, wherein a composite of acceptability measures from each module is input to a state classification and decision system to diagnose specific source of said error.

49. The system of claim 48, further comprising a database of corrective instructions.

50. A method for detecting errors in spectroscopic measurement of blood and/or tissue analytes comprising the steps of:
   measuring at least one spectrum at a selected tissue site on a subject;
   applying one or more individual methods for detecting errors in spectral measurements to said measured spectrum, wherein said methods are implemented individually, in subsystems according to a commonality among selected methods, or in a hierarchy wherein a level of said hierarchy implements any of: at least one method, at least one subsystem, and a combination of at least one method and at least one subsystem;
   collecting output of said methods;
   detecting conditions inconsistent with analyte determination based on said output;
   recording generated errors; and
   reporting a decision regarding acceptability of a measurement.

51. The method of claim 50, further comprising the steps of:
   outputting an acceptability measure by each method; and
   defining a range of acceptability for each acceptability measure wherein ranges of acceptability are based on a set of exemplary samples, the set including both erroneous measurements of known origin and valid measurements; and generating an error when an acceptability measure is outside of its associated range of acceptability.

52. The method of claim 50, wherein said analyte comprises glucose.

53. The method of claim 50, further comprising the step of:

processing raw spectra, spectra including sample spectra and reference spectra;

averaging processed intensity spectra;

calculating an absorbance spectrum from said processed intensity spectra;

preprocessing said absorbance spectrum;

extracting features from a preprocessed absorbance spectrum;

generating a tissue template set, the tissue template comprising a set of measurements taken at onset of a measurement period; and providing a calibration model, said calibration model applied to any of said preprocessed absorbance spectrum and extracted features to measure said analyte, said calibration model also applied to estimate relative precision of a measurement and/or determine certainty of a measurement in view of past measurements.

54. The method of claim 53, wherein processing raw spectra comprises:

subtracting an electrical offset from said raw intensity spectra.

55. The method of claim 53, wherein averaging comprises the steps of:

calculating a simple average; and producing a robust estimation of mean intensity at each wavelength.

56. The method of claim 53, wherein said absorbance spectrum comprises a specific set of wavelengths in the near IR region that has been optimized for feature extraction and measurement.

57. The method of claim 53, wherein preprocessing comprises:

scaling;

normalizing;

smoothing;

derivatizing;

filtering; and transformations that attenuate noise and instrumental variation without unduly affecting signal of interest.

58. The method of claim 53, wherein said features include any of:

simple features, comprising values of a processed spectral measurement at which slope equals zero;

derived features, comprising additional features derived from simple features through mathematical transformation; and abstract features developed through linear and/or nonlinear transformations of said preprocessed spectrum.

59. The method of claim 58, wherein simple features include any of:

critical points;

normalization points;

fat band points;

protein band points; and water band points.

60. The method of claim 59, wherein derived features are mathematically derived from said critical, normalization, fat band, protein band, and water band points.

61. The method of claim 58, wherein abstract features do not have a specific interpretation related to a physical system, abstract features including scores from a principal components analysis.

62. The method of claim 53, wherein said tissue template set includes any of:

intensity spectra for sample and reference;

an absorbance spectrum;

a preprocessed absorbance spectrum;

and a set of extracted features.

63. The method of claim 50, wherein said outputs constitute acceptability measures, and wherein said step of collecting said outputs comprises:

inputting said acceptability measures to a state classification and rule-based decision system.

64. The method of claim 63, further comprising the step of:

normalizing said acceptability measures;

determining at least one operating state for each of said levels; and making a decision regarding acceptability of an analyte measurement based on said determined operating states.

65. The method of claim 64, wherein the step of determining at least one operating state for each of said levels comprises the step of:

providing a classifier, wherein said classifier is developed from a data set of exemplar spectral measurements from a representative population sample.

66. The method of claim 65, the step of determining at least one operating state further comprising the step of:

defining classes by assigning said measurements from said data set to classes.

67. The method of claim 66, wherein the step of defining classes comprises:

defining classes through known differences in the data, based on a supervised approach.

68. The method of claim 66, wherein the step of defining classes comprises:

exploring and developing clusters of the data in feature space, wherein class definition employs an unsupervised approach, wherein said acceptability measures are used to, so that within cluster homogeneity and between cluster separation is optimized.

69. The method of claim 68, wherein a large set of samples from a multiplicity of subjects is used to create a database, the database including acceptability measures, measurements, and reference measurements.

70. The method of claim 68, wherein acceptability measures are sorted according to level of sophistication.

71. The method of claim 68, wherein the step of defining classes further comprises:

performing an abstract factor analysis to account for redundancy of information presented by said acceptability measures; and performing a cluster analysis to identify classes, said classes constituting states, associated with various levels of measurement error.

72. The method of claim 71, further comprising the step of
combining states to provide an error diagnosis.

73. The method of claim 65, wherein said data set is created through introduction of errors associated with defined categories, and wherein a statistical classifier is used to map said acceptability measures to a final decision.

74. The method of claim 73, wherein said classifier is designed by determining an optimal mapping from feature space to a class estimate that minimizes misclassifications.

75. The method of claim 65, wherein statistically based class definitions provide crisp class definitions.

76. The method of claim 65, wherein class assignment and decisions are based on fuzzy set theory.

77. The method of claim 76, wherein membership in fuzzy sets is defined by a continuum of grades and a set of membership functions that map feature space into an interval for each class, wherein assigned membership grade represents a degree of class membership, so that a sample can simultaneously be a member of more than one class.

78. The method of claim 50, wherein said individual methods include any of:
an online error check method;
an instrument error-detection method;
an instrument QC (quality control)-checking method;
a signal-processing method;
a sampling error-detection method;
a spectral anomaly-detection method;
surface contact error-detection method;
a hydration-checking method;
a sample variation-detection method;
a sample transient-detection method;
a patient skin temperature-measuring method;
a sample consistency-assessment method;
a sample stability-assessment method;
a tissue transient-detection method;
a skin temperature transient-detection method;
a data consistency method;
a sample structure variation-detection method;
an instrument drift-monitoring method;
an instrument stability-monitoring method;
an instrument performance-monitoring method;
a classification method;
a calibration set-comparison method;
an instrument operation-comparison method;
a measurement precision-estimation method;
a measurement range-assessment method; and
an expected value-prediction method.

79. The method of claim 78, wherein said online error check method comprises the step of:
determining whether proper material has been scanned and whether material characteristics are similar to previously set standards.

80. The method of claim 78, wherein said instrument error-detection method comprises the step of:
detecting errors based on a series of tests that evaluate signal levels compared to a target range at particular wavelengths indicative of failure modes.

81. The method of claim 78, wherein failure modes include any of:
illumination system failure;
excessive instrument temperature;
damaged illumination/detection elements; and
excessive changes in light intensity.

82. The method of claim 78, wherein the instrument QC method comprises the step of:
determining if the instrument is operating according to instrument specifications and reporting an error if not.

83. The method of claim 78, wherein said specifications include specifications for any of:
instrument noise (at each wavelength and overall);
peak signal level; and
x-axis variation.

84. The method of claim 78, wherein said signal-processing method comprises any of the steps of:
applying baseline correction;
applying ensemble averaging;
applying wavelength standardization;
applying finite impulse response filtering (FIR);
differentiating;
applying multiplicative scatter correction;
applying standard normal transformation; and
calculating absorbance;
wherein all scanned materials are processed into a set of spectra that can be used to perform error detection and measure blood glucose.

85. The method of claim 78, wherein said sampling error-detection method comprises the step of:
detecting gross sampling errors, gross sampling errors including any of:
lifting or moving body part bearing measurement site during scanning;
moving a reference during scanning; and
improper application of a coupling medium.

86. The method of claim 78, wherein said spectral anomaly detection method comprises the step of:
detecting changes in relative absorbance of constituents at various depths corresponding to modification of a sampled tissue volume.

87. The method of claim 78, wherein said surface contact error detection method comprises the steps of:
extracting spectral features related to surface contact and comparing said extracted features to related features from a tissue template spectrum, wherein an error condition results if surface contact deviates significantly from said tissue template or from an a priori level.

88. The applying of claim 78, wherein said hydration-checking method comprises the steps of:
extracting spectral features related to sample hydration;
comparing said extracted features to features from a tissue template and previously calculated features; and
reporting an error condition if patient's hydration has changed significantly from that of tissue template.

89. The method of claim 78, wherein said sample variation-detection method comprises the step of:
detecting mechanical distortion of an optically sampled tissue volume, wherein extracted features from a sample spectrum are compared to features from a tissue template by means of a distance measure, and reporting an error if said sample spectrum exceeds a pre-set limit.

90. The method of claim 78, wherein said sample transient-detection method comprises the step of:

detecting rapid changes in coupling between a patient interface module and sample site, or rapid change in the sample by comparing extracted features with a previously established library representing a plurality of error conditions, error conditions including:

arm movement while scanning;

perspiration;

excessive pressure;

poor patient-instrument coupling;

tissue distortion;

tissue heating;

rapid changes in patient physiology;

fluid displacement in the tissue; and poor sampling conditions.

91. The method of claim 78, wherein said patient skin temperature-measuring method comprises either of the steps of:

detecting patient skin temperature through a direct measurement with a skin temperature probe; or detecting patient skin temperature spectroscopically based on a predetermined skin temperature calibration model;

wherein the skin temperature is compared to skin temperature associated with a tissue template, and temperatures that vary from a target range produce an error condition.

92. The method of claim 78, wherein said sample consistency-assessment method comprises the step of:

comparing a sample spectrum with prior patient scans and calculating similarity;

wherein an error condition results if the sample spectrum differs substantially from the prior scans.

93. The method of claim 78, wherein said sample stability-assessment module comprises the step of:

comparing level of analyte marker bands with pre-set limits by comparing a processed sample spectrum with a tissue template spectrum over a selected wavelength range and calculating similarity between the two spectra;

wherein an error condition results if the sample spectrum differs substantially from the tissue template.

94. The method of claim 78, wherein said tissue transient-detection method comprises the step of:

examining time history of sample spectra features related to any of:

changes in physiological state;

changes in local tissue morphology; and patient-instrument coupling errors;

wherein an error condition occurs if range and time-related correlation of a feature exceeds a predetermined limit.

95. The method of claim 78, wherein said skin temperature transient-detection method comprises the step of:

comparing range and time correlation of measured skin temperature over samples collected subsequent to collecting a tissue template, wherein a sample that is either out of range or that displays a unidirectional temperature change results in an error condition.

96. The method of claim 78, wherein said data consistency method comprises the step of:

comparing sample spectra with historical data;

wherein an error condition results if variability within the sample spectrum is inconsistent with said historical data.

97. The method of claim 78, wherein said sample structure variation-detection method comprises the step of:

comparing a tissue fingerprint of a newly collected sample spectrum with that of an original stored tissue template, said tissue fingerprint comprising a plurality of distinct features related to analyte absorption;

wherein an error condition results if the newly collected sample spectrum differs substantially from said tissue template, an error indicating a gross change in sampled tissue volume.

98. The method of claim 78, wherein said instrument drift-monitoring method comprises the step of:

comparing performance parameters with data collected with a tissue template;

wherein an error condition results if an instrument is outside of normal instrument operating procedures.

99. The method of claim 78, wherein said instrument stability-monitoring method comprises the step of:

comparing sample spectra with data from a history file containing instrument parameters, parameters including any of RMS (root mean squared) noise, wavelength shift and signal intensity;

wherein an error condition occurs if instrument performance has changed over a short time period.

100. The method of claim 78, wherein said instrument performance-monitoring method comprises the step of:

predicting potential instrument-related failure based on monitoring changes in any of instrument noise, temperatures, wavelength stability, and signal intensity over life of the instrument.

101. The method of claim 78, wherein said classification method comprises the step of:

determining a suitable patient class for calibration on the basis of a calibration database;

wherein sample spectral falling outside a classified set are classed as outliers so that an error conditions results.

102. The method of claim 78, wherein said calibration set-comparison method comprises the step of:

comparing a sample spectrum with a calibration set using any of feature extraction and cluster analysis to determine consistency of the sample spectrum with spectral data used to generate a calibration model, wherein spectra falling outside a range of calibration create an error condition.

103. The method of claim 78, wherein said instrument operation-comparison method comprises the step of:

comparing operational state of the instrument with similar instruments, including an instrument used to collect calibration data, wherein history information from said similar instruments is pooled to compare characteristics of the instrument with the similar instruments.

104. The method of claim 78, wherein said measurement precision-estimation method comprises the step of:

applying a calibration model to each of a set of tissue absorbance replicates to compare any of range, trend and standard deviation of glucose measurements based on said replicates with a maximum acceptable value;

wherein measurements exceeding said value are rejected, so that a confidence estimate of a final, averaged glucose measurement is produced.

105. The method of claim 78, wherein said measurement range-assessment method comprises the step of:

averaging glucose measurements associated with a set of replicate spectral scans to yield a final glucose measurement;

wherein an error condition results if said final measurement is outside a preset range.

106. The method of claim 78, wherein said expected value-prediction method comprises the steps of:

applying a prediction module to predict erroneous glucose measurements, wherein said prediction model uses a time series of past glucose measurements to extrapolate a future prediction; and comparing said predication with a measurement based on a newly acquired sample spectrum;

wherein an error results if a large discrepancy exists between the measurement from the newly acquired spectrum and the prediction, where the prediction has a high degree of certainty.

107. The method of claim 78, wherein subsystems are defined according to sophistication of included methods, said subsystems including any of:

a low-level subsystem;

a mid-level subsystem; and a high-level subsystem.

108. The method of claim 107, wherein said low-level subsystem includes methods for testing data immediately after collection of reference and sample spectra, said spectra comprising intensity spectra.

109. The method of claim 107, wherein testing is based on acceptability specifications for noninvasive glucose measurement, and wherein an action resulting from deviation from a specified level of acceptability includes any of:

rejection of a collected spectrum;

rejection of a tissue sample; and generation of an instrument malfunction error.

110. The method of claim 107, wherein said low-level subsystem includes any of:

the online error check method;

the instrument error detection method;

the instrument QC-checking method;

the signal processing method; and the sampling error detection method.

111. The method of claim 107, wherein a system manager inputs instrument performance specifications and target spectra for each type of material to be scanned to said low-level subsystem.

112. The method of claim 111, wherein said specifications include any of:

noise limits;

minimum operating temperature limits;

maximum signal levels;

wavelength accuracy limits; and precision limits.

113. The method of claim 107, wherein actions taken by said low-level subsystem include any of:

sample rejection; and instrument QC check.

114. The method of claim 107, wherein said mid-level subsystem comprises a plurality of sublevels, said sublevels corresponding to type of information necessary for analysis.

115. The method of claim 107, wherein said mid-level subsystem uses a tissue template to determine if instrument performance and/or a sampled tissue volume have changed relative to an earlier time.

116. The system of claim 107, wherein said mid-level subsystem includes any of:

the spectral anomaly-detection method;

the surface contact error-detection method;

the hydration-checking method;

the sample variation-detection method;

the sample transient-detection method;

the patient skin temperature-measuring method;

the sample consistency-assessment method;

the sample stability-assessment method;

the tissue transient-detection method;

the skin temperature transient-detection method;

the data consistency method;

the sample structure variation-detection method;

the instrument drift-monitoring method;

the instrument stability-monitoring method; and the instrument performance-monitoring method.

117. The method of claim 107, wherein actions taken by said mid-level subsystem include any of:

instrument maintenance;

recollect tissue template;

sample rejection; and instrument QC check.

118. The method of claim 107, wherein said high-level subsystem relies on:

a calibration model and parameters relating to the calibration model;

a patient database;

patient history;

a tissue template; and measurement specifications common to all instruments and all patients.

119. The method of claim 107, wherein said high-level subsystem includes any of:

the classification method;

the calibration set-comparison method;

the instrument operation-comparison method;

the measurement precision-estimation method;

the measurement range-assessment method; and the expected value-prediction method.

120. The method of claim 107, wherein actions taken by said high-level subsystem include any of:

change calibration model;

recalibrate patient;

instrument failure;

invalid glucose measurement;

instrument maintenance;

recollect tissue template;

sample rejection; and instrument QC check.

121. The method of claim 107, wherein levels of said hierarchic system receive and inherit information from lower levels.

122. The method of claim 121, wherein errors generated at each level are inherited by succeeding levels for error diagnosis until a critical error is encountered.

123. The method of claim 121, wherein a composite of acceptability measures from each module is input to a state classification and decision system to diagnose specific source of said error.

124. The method of claim 123, further comprising the step of:

providing corrective instructions from a database of corrective instructions.

* * * * *